(12) United States Patent
Hynynen et al.

(10) Patent No.: US 12,290,403 B2
(45) Date of Patent: *May 6, 2025

(54) SYSTEMS AND METHODS FOR PERFORMING TRANSCRANIAL ULTRASOUND THERAPEUTIC AND IMAGING PROCEDURES

(71) Applicant: SUNNYBROOK RESEARCH INSTITUTE, Toronto (CA)

(72) Inventors: Kullervo Hynynen, Toronto (CA); Alec Hughes, Mississauga (CA); Lulu Deng, Toronto (CA); Meaghan O'Reilly, Scarborough (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/377,460

(22) Filed: Oct. 6, 2023

(65) Prior Publication Data

US 2024/0041429 A1   Feb. 8, 2024

Related U.S. Application Data

(63) Continuation of application No. 17/367,745, filed on Jul. 6, 2021, now Pat. No. 11,793,490, which is a (Continued)

(51) Int. Cl.
*A61B 8/00* (2006.01)
*A61B 8/08* (2006.01)
(Continued)

(52) U.S. Cl.
CPC .......... *A61B 8/4494* (2013.01); *A61B 8/0808* (2013.01); *A61B 8/4477* (2013.01);
(Continued)

(58) Field of Classification Search
CPC ... A61B 8/4494; A61B 8/0808; A61B 8/4477; A61B 8/5207; A61B 34/10; A61B 90/50;
(Continued)

(56) References Cited

U.S. PATENT DOCUMENTS 8,292,835 B1 * 10/2012 Cimino .................... A61N 7/02
601/3
11,071,522 B2 * 7/2021 Hynynen ............... A61B 90/50
(Continued)

FOREIGN PATENT DOCUMENTS

CN   104545919 A  *  4/2015  .......... A61B 5/0042

OTHER PUBLICATIONS

Sun et al., "The potential of transskull ultrasound therapy and surgery using the maximum available skull surface area", 1999 (Year: 1999).*

(Continued)

*Primary Examiner* — Adil Partap S Virk
(74) *Attorney, Agent, or Firm* — Aird & McBurney LP

(57) ABSTRACT

Systems and methods are provided for performing transcranial diagnostic procedures using a transcranial ultrasound transducer array. The array elements are positioned and oriented such that far field regions respectively associated therewith spatially overlap within the brain of a patient. The array elements may be oriented approximately normal to the skull, permitting efficient coupling of ultrasound energy into the brain. The array elements are controlled to generate ultrasound pulses, where the timing of the pulses is controlled, based on registration between the array elements and volumetric image data, such that ultrasound energy is focused at a target within spatially overlapping far fields of the array elements. The transcranial ultrasound transducer array elements may be positioned and oriented relative to the (Continued)

skull such that their respective ultrasound beams are focused within the skull and diverging with the brain.

16 Claims, 25 Drawing Sheets

Related U.S. Application Data continuation of application No. 15/852,862, filed on Dec. 22, 2017, now Pat. No. 11,071,522.

(60) Provisional application No. 62/438,283, filed on Dec. 22, 2016.

(51) Int. Cl.
    *A61B 34/10*     (2016.01)
    *A61B 90/50*     (2016.01)
    *A61N 7/00*     (2006.01)
    *A61N 7/02*     (2006.01)

(52) U.S. Cl.
    CPC .......... *A61B 8/5207* (2013.01); *A61B 34/10* (2016.02); *A61B 90/50* (2016.02); *A61N 7/00* (2013.01); *A61B 8/54* (2013.01); *A61B 2034/108* (2016.02); *A61B 2090/502* (2016.02); *A61N 2007/0021* (2013.01); *A61N 2007/0052* (2013.01); *A61N 2007/0073* (2013.01); *A61N 2007/0078* (2013.01); *A61N 2007/0095* (2013.01); *A61N 2007/027* (2013.01)

(58) Field of Classification Search
CPC ............. A61B 8/54; A61B 2034/108; A61B 2090/502; A61B 8/4209; A61B 8/52; A61B 2034/105; A61N 7/00; A61N 2007/0021; A61N 2007/0052; A61N 2007/0073; A61N 2007/0078; A61N 2007/0095; A61N 2007/027; A61N 7/02
See application file for complete search history.

(56) References Cited

U.S. PATENT DOCUMENTS

| | | | | |
|---|---|---|---|---|
| 11,793,490 | B2* | 10/2023 | Hynynen | A61B 8/4494 |
| 2003/0092987 | A1* | 5/2003 | Hynynen | A61N 7/02 |
| | | | | 600/437 |
| 2004/0049134 | A1* | 3/2004 | Tosaya | A61H 23/0236 |
| | | | | 601/2 |
| 2006/0241459 | A1* | 10/2006 | Tai | A61B 8/0808 |
| | | | | 600/437 |
| 2008/0009739 | A1* | 1/2008 | Chiang | G01S 7/5208 |
| | | | | 600/459 |
| 2009/0230823 | A1* | 9/2009 | Kushculey | B06B 1/0637 |
| | | | | 310/366 |
| 2010/0268088 | A1* | 10/2010 | Prus | A61N 7/02 |
| | | | | 600/459 |
| 2011/0319793 | A1* | 12/2011 | Hynynen | A61N 7/02 |
| | | | | 601/2 |
| 2012/0083718 | A1* | 4/2012 | Alleman | A61B 8/4427 |
| | | | | 601/2 |
| 2012/0083719 | A1* | 4/2012 | Mishelevich | A61N 7/00 |
| | | | | 601/2 |
| 2012/0283502 | A1* | 11/2012 | Mishelevich | A61N 2/006 |
| | | | | 601/2 |
| 2012/0289869 | A1* | 11/2012 | Tyler | A61N 7/00 |
| | | | | 601/2 |
| 2013/0060146 | A1* | 3/2013 | Yang | G01B 11/25 |
| | | | | 600/476 |
| 2013/0144192 | A1* | 6/2013 | Mischelevich | A61N 7/00 |
| | | | | 601/2 |
| 2015/0148675 | A1* | 5/2015 | Haupt | A61B 8/488 |
| | | | | 600/438 |
| 2016/0243381 | A1* | 8/2016 | Alford | A61N 7/00 |
| 2017/0188992 | A1* | 7/2017 | O'Brien | A61B 8/488 |
| 2018/0000351 | A1* | 1/2018 | Zharov | G01N 15/1434 |
| 2024/0041429 | A1* | 2/2024 | Hynynen | A61B 8/4477 |

OTHER PUBLICATIONS

Clement et al., "Investigation of a large-area phased array for focused ultrasound surgery through the skull", 2000 (Year: 2000).*
Clement et al., "A non-invasive method for focusing ultrasound through the human skull", 2002 (Year: 2002).*
Aarnio et al., "A New Ultrasound Method For Determining The Acoustic Phase Shifts Cause By The Skull Bone", 2005 (Year: 2005).*
McDannold et al., "Transcranial Magnetic Resonance Imaging-Guided Focused Ultrasound Surgery of Brain Tumors: Initial Findings in 3 Patients", 2010 (Year: 2010).*
CN104545919 English Translation (Year: 2015).*

* cited by examiner

| Material | $\rho$ (kg m$^{-3}$) | $c_L$ (m s$^{-1}$) | $\alpha_L$ (Np m$^{-1}$) |
|---|---|---|---|
| Water | 1000 | 1500 | 0 |
|  | $\kappa$ (W °C$^{-1}$ m$^{-1}$) | $C$ (J kg$^{-1}$ °C$^{-1}$) | W (s$^{-1}$) |
| Water | 0.62 | 4180 | 0 |
| Skull | 0.43 | 1440 | $3.33 \times 10^{-4}$ |
FIG. 4
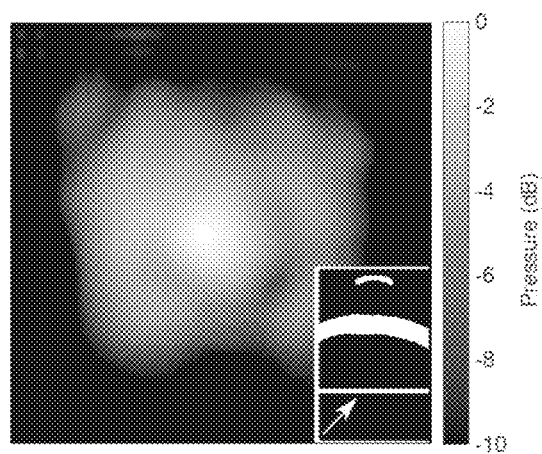
FIG. 5A
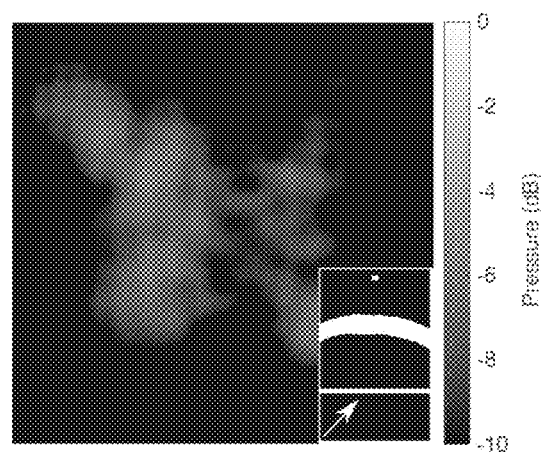
FIG. 5B a non-conformal hemisphere - solid ( _____ )

b conformal arrangement of flat array elements - short dash ( __ __ __ )

c conformal arrangement of focused transducer elements - long dash ( __ __ __ )

| Elements | Focal Length (mm) | f-number |
|---|---|---|
| 64 | 11 | 0.61 |
| 128 | 9 | 0.75 |
| 256 | 8 | 1.0 |
| 512 | 7 | 1.2 |

FIG. 11A

| | Inner | Mid | Outer |
|---|---|---|---|
| Focal Length (mm) | 16 | 13 | 12 |
| f-Number | 0.73 | 0.59 | 0.55 |
| Peak Pressure (kPa) | 130 | 131 | 118 |
| -3dB Volume (cm$^3$) | 0.0229 | 0.0228 | 0.0170 |
| -6dB Volume (cm$^3$) | 4.02 | 0.65 | 0.68 |

FIG. 11B

SYSTEMS AND METHODS FOR PERFORMING TRANSCRANIAL ULTRASOUND THERAPEUTIC AND IMAGING PROCEDURES

CROSS-REFERENCE TO RELATED APPLICATION

This application claims priority to U.S. Provisional Application No. 62/438,283, titled "SYSTEMS AND METHODS FOR PERFORMING TRANSCRANIAL ULTRASOUND THERAPEUTIC AND IMAGING PROCEDURES" and filed on Dec. 22, 2016, the entire contents of which is incorporated herein by reference.

BACKGROUND

The present disclosure relates to ultrasound-based therapy and imaging. More particularly, the present disclosure relates to transcranial ultrasound systems and methods.

The application of focused ultrasound to the brain through the intact skull has a long history leading up to the clinical implementations of the present day. Since the first successful ablation of animal brain tissue transcranially using a single transducer in 1980, to the present day multi-center clinical trials of Magnetic Resonance (MR)-guided focused ultrasound for the treatment of essential tremor using hemispherical phased arrays consisting of more than one thousand elements, new phased array designs have been conceptualized to overcome previous challenges, such as skull aberration correction, standing wave reduction, skull heating, and dual-frequency blood-brain barrier disruption.

Most of the current clinical work in transcranial focused ultrasound involves continuous wave ultrasound to cause thermal ablation. Early studies showed that pulsed ultrasound could be used for blood-brain barrier disruption. This has led to studies involving blood-brain barrier disruption in conjunction with drug delivery to treat Alzheimer's disease and deliver immune cells to metastatic brain tumors, among others. In these applications, skull heating is of minimal concern due to the low duty cycle, and tight focusing and energy delivery is of the highest importance. A recent study has even shown that mechanical tissue destruction is possible with lower intensity pulsed ultrasound when used in conjunction with microbubbles.

However, despite these successes, transcranial ultrasound implementations have met with challenges due to the acoustic properties of the skull. For example, one problem that is encountered when transmitting ultrasound through a human skull for therapeutic, diagnostic or monitoring purposes is the high acoustic impedance of the skull bone compared to surrounding soft tissues. This acoustic impedance mismatch between the skull and surrounding soft tissues causes a significant amount of the acoustic energy to be reflected at both skull bone surfaces.

The maximum transmission through the skull occurs when the ultrasound beam enters the skull at normal incidence, with a steep reduction in the transmission as the entrance angle is increased, such that longitudinal waves are not capable of transmission through the skull beyond angles of approximately 25-30°. When the angle of incidence is high, the incident longitudinal waves will be converted to shear waves, and these shear waves can propagate through the bone at larger angles. However, the shear waves are attenuated much faster that the longitudinal waves in the bone. Therefore, it is difficult to utilize the whole skull surface area for off-center target sonications.

SUMMARY

Systems and methods are provided for performing transcranial diagnostic procedures using a transcranial ultrasound transducer array. The array elements are positioned and oriented such that far field regions respectively associated therewith spatially overlap within the brain of a patient. The array elements may be oriented approximately normal to the skull, permitting efficient coupling of ultrasound energy into the brain. The array elements are controlled to generate ultrasound pulses, where the timing of the pulses is controlled, based on registration between the array elements and volumetric image data, such that ultrasound energy is focused at a target within spatially overlapping far fields of the array elements. The transcranial ultrasound transducer array elements may be positioned and oriented relative to the skull such that their respective ultrasound beams are focused within the skull and diverging with the brain.

Accordingly, in a first aspect, there is provided a system for performing diagnostic or therapeutic transcranial ultrasound procedures, the system comprising:
   a support frame configured to be positioned around the head of a patient;
   a plurality of transcranial ultrasound transducer array elements supported by said support frame, wherein said plurality of transcranial ultrasound transducer array elements are supported in pre-selected positions and orientations relative to said support frame for transmitting ultrasound though a skull of the patient, such that far field regions respectively associated with said plurality of transcranial ultrasound transducer array elements spatially overlap within a far field overlap region located within a brain of the patient when said support frame is placed around the head of the patient;
   control and processing hardware operably connected to said plurality of transcranial ultrasound transducer array elements, wherein said control and processing hardware is configured to:
      control said plurality of transcranial ultrasound transducer array elements to generate an ultrasound pulse from each transcranial ultrasound transducer array elements, and control the timing of the ultrasound pulses, based on registration data spatially registering the pre-selected positions and orientations of said plurality of transcranial ultrasound transducer array elements with volumetric image data associated with the patient, such that ultrasound energy is focused at a pre-selected region within the far field overlap region.

In another aspect, there is provided a method of fabricating a transcranial ultrasound apparatus for performing transcranial ultrasound procedures, the method comprising:
   obtaining volumetric image data associated with the head of a patient;
   calculating, based on the volumetric image data, positions and orientations of a plurality of transcranial ultrasound transducer array elements relative to a skull of the patient, such that far field regions respectively associated with said plurality of transcranial ultrasound transducer array elements spatially overlap within a far field overlap region located within a brain of the patient;
   supporting the plurality of transcranial ultrasound transducer array elements on a support frame configured to be positioned around the head of the patient, such that said plurality of transcranial ultrasound transducer array elements are supported according to said positions and orientations.

In another aspect, there is provided a method for performing a transcranial ultrasound procedure, the method comprising:

providing a support frame configured to be positioned around the head of a patient, said support frame comprising a plurality of transcranial ultrasound transducer array elements supported thereon, wherein said plurality of transcranial ultrasound transducer array elements are supported in pre-selected positions and orientations relative to said support frame for transmitting ultrasound though a skull of the patient, such that far field regions respectively associated with said plurality of transcranial ultrasound transducer array elements spatially overlap within a far field overlap region located within a brain of the patient;

controlling said plurality of transcranial ultrasound transducer array elements to generate an ultrasound pulse from each transcranial ultrasound transducer array elements, and controlling the timing of the ultrasound pulses, based on registration data spatially registering the pre-selected positions and orientations of said plurality of transcranial ultrasound transducer array elements with volumetric image data associated with the patient, such that ultrasound energy is focused at a pre-selected region within the far field overlap region.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 4 is a table summarizing the parameters employed when performing simulations of acoustic and thermal fields.

FIGS. 5A-B plot ultrasound fields from (A) a focused and (b) a small $\lambda/2$ flat transducer, after propagation through the skull.

FIG. 11A is a table describing the array configurations employed in the simulations.

FIG. 11B is a table describing the effect of various focusing depths of the transcranial ultrasound transducer elements at an intracranial far-field focusing location 60 mm anterior to the natural focus.

DETAILED DESCRIPTION

Figure 1A:
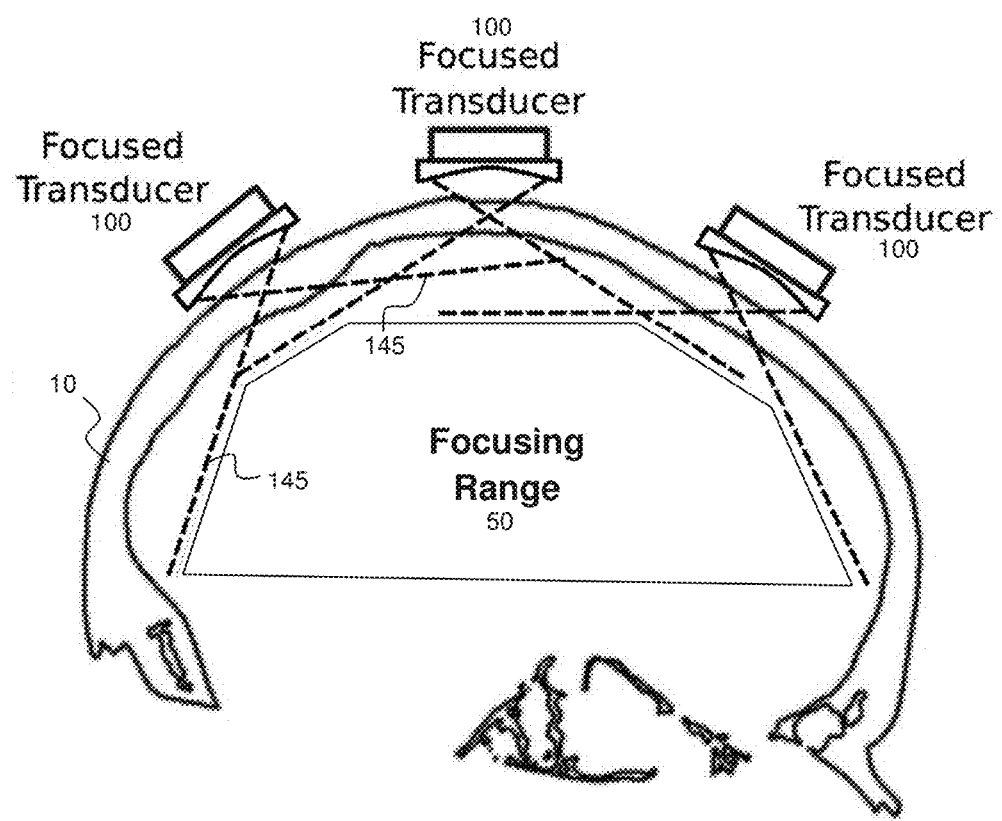
FIG. 1A illustrates an example embodiment in which transcranial ultrasound transducer array elements are supported relative to the skull by a support frame, where the ultrasound beams from the transcranial ultrasound transducer array elements are emitted such they are individually defocused in the far field, while overlapping in the far field to generate a focus.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As described above, transcranial ultrasound arrays have met with challenges in achieving off-center target sonications (e.g. targets that are more than 2-4 cm away from the center of the brain) due to the high acoustic impedance of the skull, which prohibits the transmission of longitudinal waves at oblique angles and confines therapeutic procedures to targets within a central region of the brain. The present disclosure addresses this problem by providing systems and methods in which a transcranial ultrasound transducer array is configured to achieve high levels of beam steering through the skull. This is achieved by positioning the transcranial ultrasound transducer array elements relative to the skull such that the far field of each ultrasound beam lies within the brain, and controlling the timing of ultrasound pulses emitted by each transducer array element such that the pulses arrive in-phase at the desired target.

Referring now to FIG. 1A, an example illustration of a transcranial ultrasound transducer array is shown in cross section. The transcranial ultrasound transducer array includes a plurality of transcranial ultrasound transducer array elements 100, which are supported relative to the head of the subject by a frame (not shown). Each transcranial ultrasound transducer array element emits a respective focused ultrasound beam, shown by the dashed lines. Although the illustration in FIG. 1A shows only three transducers for illustrative purposes, a transcranial device will preferably include many more than three elements in order to achieve suitable focusing, as described further below.

As illustrated in the example embodiment shown in FIG. 1A, each transcranial ultrasound transducer array element 100 is positioned such that its respective focus lies within the skull. This is more clearly shown in FIG. 1B, which shows the focusing of a single transcranial ultrasound transducer array element 100 (shown as comprising an active transducer portion 102 and an optional backing 104) to a focal region 120 within the skull 10. By focusing the ultrasound beams within the skull, the near field region 130 of each beam is localized within or near the skull, with the result that the portion of the beam that extends within the brain is in the far field. This is shown in FIG. 1A, where the transcranial ultrasound transducer array elements 100 are focused such that their respective ultrasound beams are diverging (shown by cone 145) within the brain, propagating within the far field. In contrast to other forms of transcranial ultrasound, the individual foci of the transcranial ultrasound transducer array elements are spatially separated, and the ultrasound beams of the transcranial ultrasound transducer array elements overlap in their respective far fields.

Figure 1B:
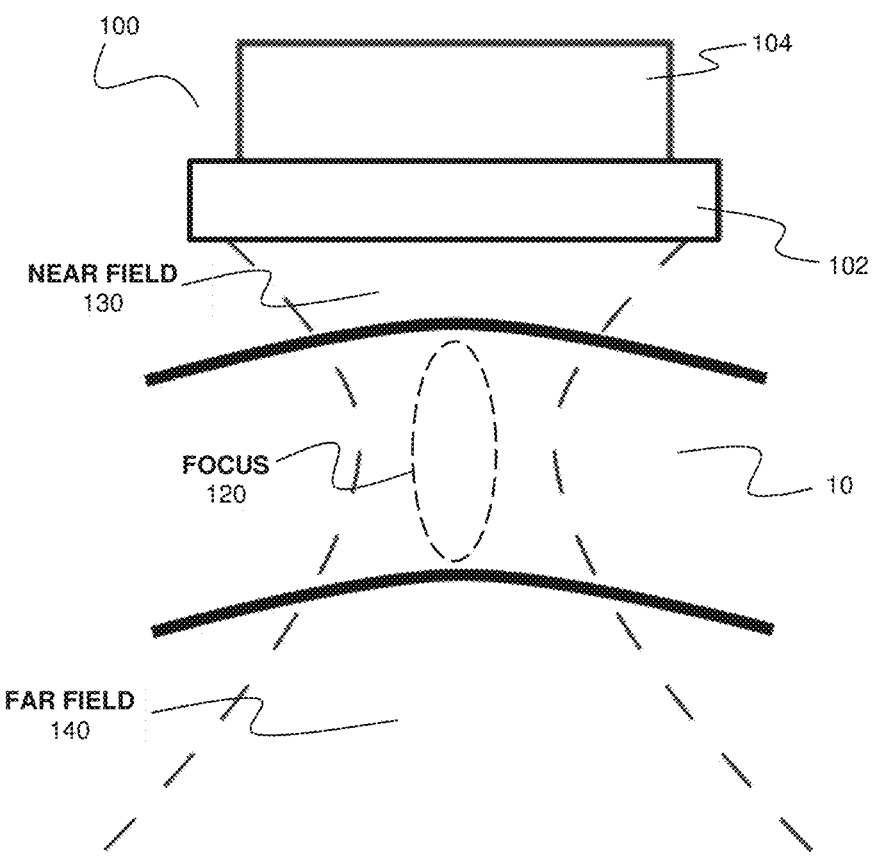
FIG. 1B illustrates an example embodiment showing the positioning and focusing of a transcranial ultrasound transducer array element relative to the skull, such that the focus of the transcranial ultrasound transducer array element lies within the skull.

As shown in FIG. 1A and FIG. 1B, the transcranial ultrasound transducer array elements 100 may be oriented such that their respective ultrasound beams enter the skull at normal incidence, or at approximately normal incidence (e.g. within ±15°). In other example implementations, the ultrasound beams may be directed toward the skull within ±10°, within ±5°, or within ±2° of normal incidence. By orienting the transcranial ultrasound transducer array elements 100 in this manner, and focusing their ultrasound beams within or near the skull, the respective ultrasound beams propagate within the skull as plane waves, and thereby enter the brain with reduced loss from impedance mismatches due to bone and tissue, and due to bone and water.

Furthermore, by orienting the transcranial ultrasound transducer array elements 100 at or near normal incidence and focusing the ultrasound beams within or near the skull, each ultrasound beam probes a small region of the skull and is thus less likely to be susceptible to the effects of inhomogeneities within the skull that can cause scattering due to local impedance mismatch and propagating effects due to local changes in the speed of sound. In other words, the propagation of each ultrasound beam through a small area of the skull having less variability in the skull density and in other properties allows for improved correction for the bone induced effects on the wave propagation.

Figure 1C:
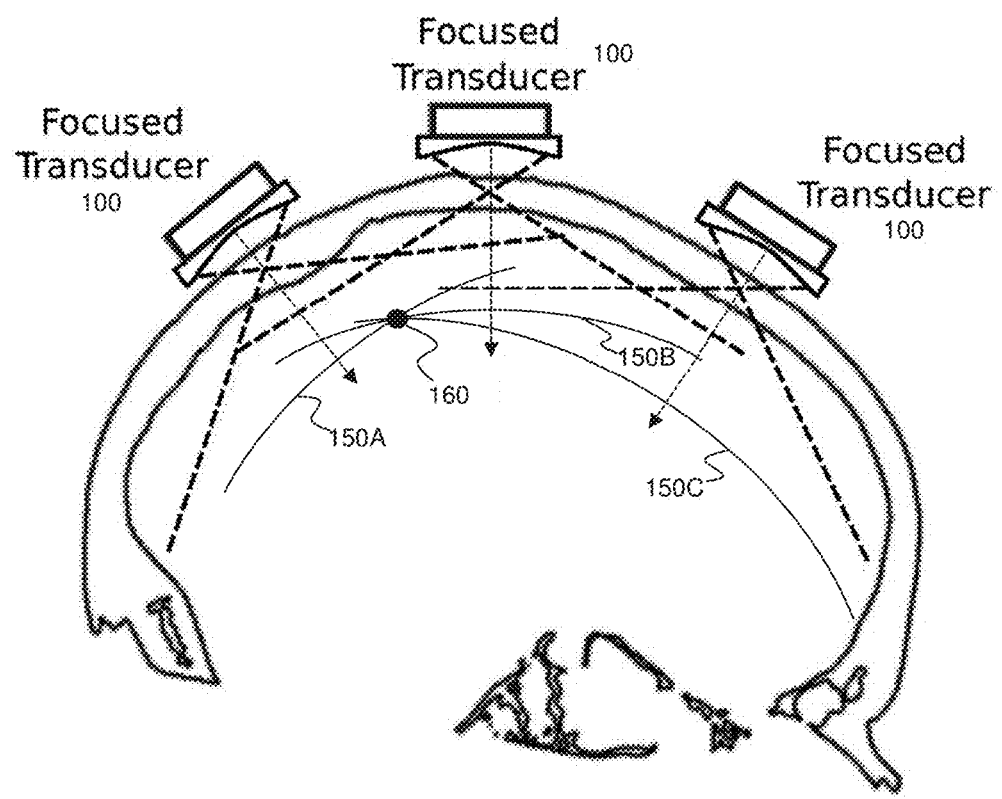
FIG. 1C illustrates the focusing of wavefronts from multiple transcranial ultrasound transducer array elements in the far field.

Referring now to FIG. 1C, the timing of the pulses (and/or phase) emitted by each transcranial ultrasound transducer array element 100 is controlled in order to generate constructive interference at or within a target region residing within the brain. In other words, by supporting a sufficient number of transcranial ultrasound transducer array elements 100 around the head, the energy from the transcranial ultrasound transducer array elements 100 can be focused into a desired target location within the brain by adjusting the phase of the ultrasound waves generated by the transcranial ultrasound transducer array elements 100 or by adjusting the timing if short bursts are transmitted by the transcranial ultrasound transducer array elements 100. This is illustrated in FIG. 1C in the case of short bursts of ultrasound waves, where the timing of the emitted pulses are controlled such that their wave fronts 150A, 150B and 150C are spatially and temporally aligned at focus 160.

As shown in FIG. 1A, each of the transcranial ultrasound transducer array elements 100 may be oriented such that all of their far field regions spatially overlap within a least a portion of the brain (shown as focusing range or focusing region 50), thereby allowing for far-field focusing within this region via control of timing of the emission of ultrasound energy from the transcranial ultrasound transducer array elements 100 (e.g. operating the transcranial ultrasound transducer array as a phased array). In some example embodiments, the focusing region 50 may lie within a portion of the brain that is known to contain a target for therapy or imaging, such as a known or suspected tumor, such that the far-field regions overlap at the target region, but need not overlap elsewhere in the brain.

Although the transcranial ultrasound transducer array elements 100 shown in FIGS. 1A and 1C are illustrated as fixed-focus concave transducers, it will be understood that one or more (e.g. all) of the transcranial ultrasound transducer array elements 100 may be phased-array transducers, henceforth referred to as a sub-array. The term "sub-array" is employed herein to clearly distinguish array elements of the transcranial ultrasound transducer array from elements of a phased array transducer that is employed as a transcranial ultrasound transducer array element of the transcranial ultrasound transducer array. The use of a phased sub-array for a transcranial ultrasound transducer array element may be beneficial in that it permits the selection of, and/or adjustment of, the focal point of the transcranial ultrasound transducer array element, without requiring mechanical repositioning of the transcranial ultrasound transducer array element.

Figure 2A:
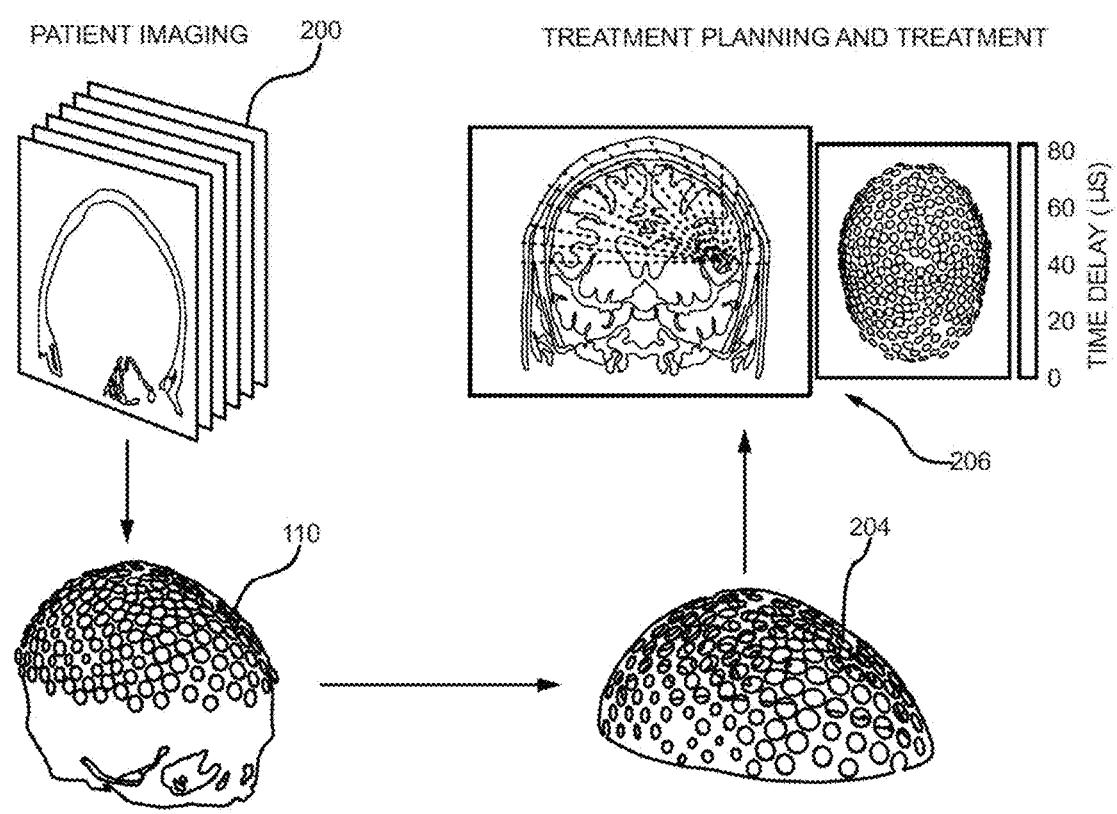
FIG. 2A illustrates an example process of design and construction a patient-specific array for transcranial focused ultrasound applications.

As described in the examples below, the use of a patient-specific spatial arrangement of the transcranial ultrasound transducer array elements may be effective in achieving a sufficiently sharp focus in the far field. FIG. 2A schematically illustrates the process of generating a patient-specific support (scaffold) for supporting the transcranial ultrasound transducer array elements, and optionally for the generation of a treatment plan for performing a transcranial focused ultrasound procedure.

As shown at 200, volumetric imaging of the patient is initially employed to determine the patient-specific skull profile. This patient-specific skull profile is then employed to determine the placement of the transcranial ultrasound transducer array elements around the head, as shown at 110. The calculated transcranial ultrasound transducer array element positions are then employed for placing the elements with the structure holding the elements or fabricate a patient-specific frame (an array support structure; scaffold) 110 that is configured to fit the patient's head. As described below, this patient-specific frame could be fabricated using rapid prototyping, and the support may include attachment interfaces for receiving and supporting the transcranial ultrasound transducer array elements. Finally, on the treatment day, the array would be fixed to the patient prior to the typical imaging sequence for target localization, followed by computer-assisted treatment planning and treatment.

The patient-specific frame 110 may include a plurality of attachment interfaces for receiving and supporting the transcranial ultrasound transducer array elements 100. For example, the attachment interfaces may be provided as apertures (recesses) into which the transcranial ultrasound transducer array elements 100 are placed. The transcranial ultrasound transducer array elements 100 may be affixed to the patient-specific frame 110 according to a wide variety of different means, such as with an attachment mechanism (e.g. via fasteners that extend into the patient-specific frame 110, optionally into pre-formed holes), or an adhesive such as a glue. The transcranial ultrasound transducer array elements may be remotely interfaced with electronics through wires or through a flexible printed circuit board. The transcranial ultrasound transducer array elements 100 may be removably attachable to the patient-specific frame 110.

The patient-specific headset may also include a coupling layer that is provided adjacent to an inner surface of the patient-specific frame. The outer surface of the coupling layer may contact distal surfaces of the transcranial ultrasound transducer array elements 100, and the inner surface of the coupling layer contacts the patient's head, thereby facilitating coupling of energy between the transducers in the patient-specific frame and the patient's head. The coupling layer may be an acoustic coupling layer that facilitates propagation of acoustic waves and reduces reflections at interfaces. In one example implementation, the coupling layer includes an elastic membrane that retains a liquid layer between the transducer surfaces and the elastic membrane, such that coupling to the skin is achieved.

The transcranial ultrasound transducer array elements, and their respective attachment interfaces, may have unique shapes (i.e. they may be respectively keyed), such that a given transcranial ultrasound transducer array element (e.g. its respective housing) fits uniquely with its respective attachment interface.

Figure 2B:
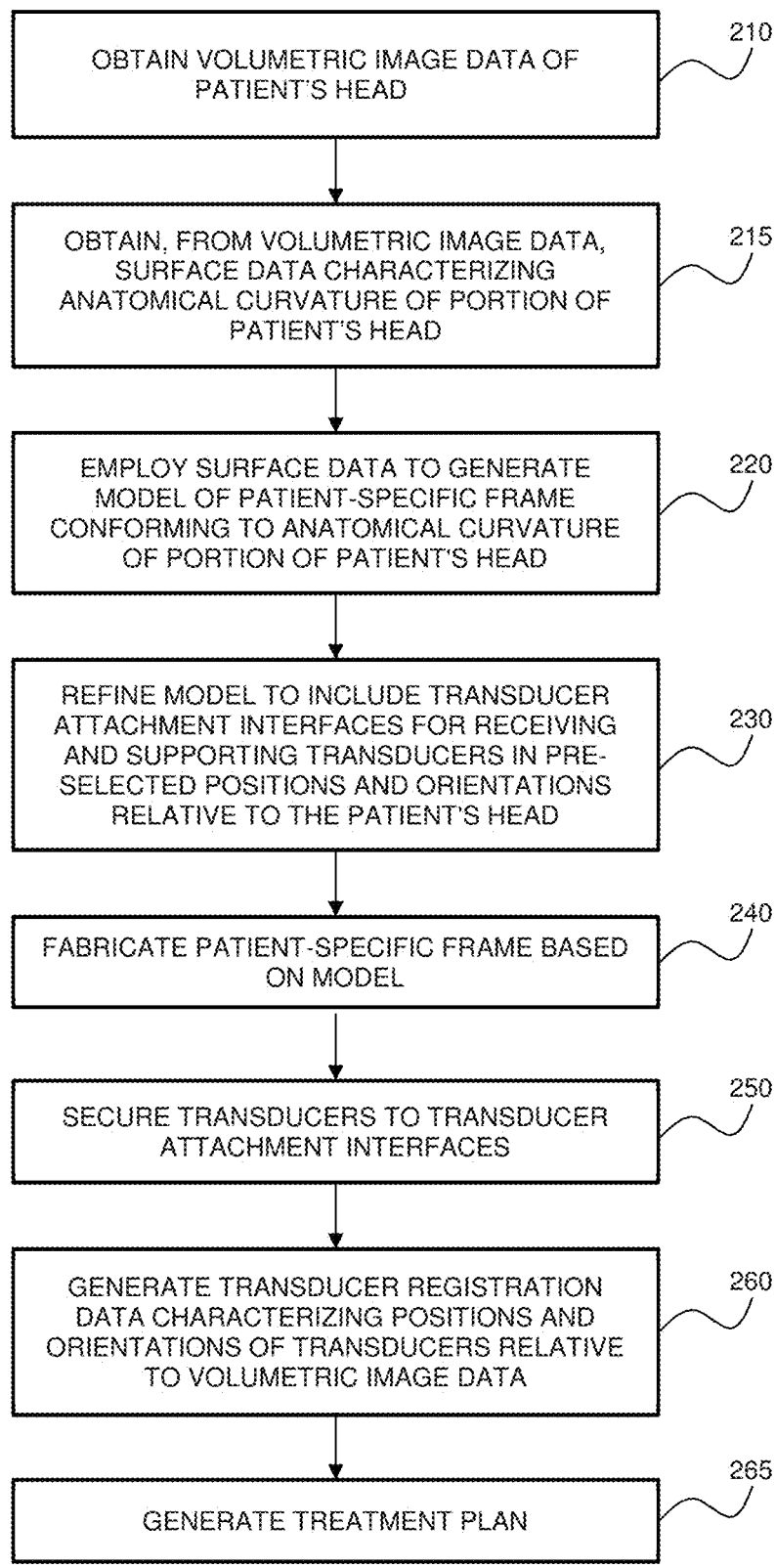
FIG. 2B is a flow chart illustrating an example method of fabricating a patient-specific headset.

As noted above, the patient-specific frame conforms to the anatomical contour of at least a portion of the patient's head. Such a conformal frame may be fabricated based on volumetric image data of the patient's head. FIG. 2B illustrates an example method for fabricating a patient-specific frame based on volumetric image data associated with the patient. In steps 210 and 215, volumetric image data of a patient's head is obtained and processed to provide surface data characterizing an anatomical curvature (e.g. skin or bone surface) of a portion of the patient's head. The volumetric data may be obtained, for example, by performing imaging using an imaging modality such as, but not limited to, magnetic resonance (MR) imaging and computed tomography (CT) imaging. The volumetric image data may be obtained based on a previously performed imaging procedure.

The volumetric image data may be processed and segmented to obtain surface data characterizing the surface of a portion of the patient's skull. Such surface segmentation may be performed, for example, using imaging processing software such as the Mimics™ software platform (Materialise, Belgium). Such software enables the creation of a 3D model (the surface data) of the surface of a portion of the patient's head. The model may be created using known techniques, such as using the steps of thresholding, region growing and manual editing. Automatic thresholding may be performed to achieve a first approximation of the skin surfaces of the skull, followed by manual editing to obtain a refined model. Haptic modeling, for example using a modeling software platform such as the PHANTOM™ Desktop Haptic Device, may be used to further refine the model. Additional example methods of image processing and segmentation of volumetric image data are disclosed in U.S. Pat. No. 8,086,336.

Subsequently, as shown in step 220, the surface data is used to produce a digital model to determine the placement of the transducer elements around the head of the patient. For example, a suitable software platform (such as the software package Surfacer™) may be employed to generate a model based on a point cloud of surface data points. This information can then be used to place the transducers, for example, when they are located in a holder that allows them to be moved in the desired locations. As shown at step 230, the model is then modified or refined (e.g. updated) to include a plurality of transducer attachment interfaces for receiving and supporting a plurality of transcranial ultrasound transducer array elements in pre-selected positions and orientations relative to the patient's head, and for supporting the transducers such that energy is coupled transcranially.

The positions and orientations of the transducer attachment interfaces may be determined as follows. Computer simulations can be used to calculate the wave propagation and select the positions from where the far-field of the transducers can reach the target location.

The digital model may be further refined to include one or more additional features, such as, but not limited to, an attachment interface for the attachment of one or more fiducial markers, an aperture to permit surgical access to a selected region of the patient's head when the patient-specific frame is worn (or otherwise placed on or around the head of the patient), markers for identifying reference directions, and one or more positioning features such as external handles.

The digital model, updated to include the transducer attachment interfaces, is then employed to fabricate the patient-specific frame, as shown at step 240. For example, the patient-specific frame may be fabricated from the model using 3D printing. In another example, the model may be employed to produce a mold suitable for forming the patient-specific frame, and the mold may be subsequently employed to fabricate the patient-specific frame.

After having fabricated the patient-specific frame, the transcranial ultrasound transducer array elements (or transducer array element assemblies or modules) are secured (attached, adhered, etc.) to the respective transducer attachment interfaces of the patient-specific frame, as shown at step 250.

In order to employ the patient-specific headset for performing diagnostic or therapeutic procedures based on pre-operative volumetric image data, a relationship may be established between the positions and orientations of the transcranial ultrasound transducer array elements and the volumetric image data (i.e. so that both can be represented within a common reference frame). Accordingly, in step 260, the known positions and orientations of the transcranial ultrasound transducer array elements (as prescribed in the digital model) are spatially registered relative to the volumetric image data, thereby generating transducer registration data characterizing the positions and orientations of the transducers relative to the volumetric image data. For example, such transducer registration data may include the spatial coordinates of the transcranial ultrasound transducer array elements, and vectors identifying their respective orientations, in the reference frame of the volumetric data. In another example implementation, the transducer registration data may include a coordinate transformation for transforming the positions and orientations of the transcranial ultrasound transducer array elements from a first reference frame to the reference frame of the volumetric image data. The transducer registration data enables the determination of the positions and orientations of the transcranial ultrasound transducer array elements relative to the volumetric image data, enabling, for example, the determination of suitable time and/or phase delays of transcranial ultrasound transducer array elements to focus, in the overlapping far field region, an energy beam at a specific location or region within the patient's head. The registration data, volumetric image data and the known positions and orientations of the transcranial ultrasound transducer array elements may then be employed to generate a treatment plan, as shown at 265.

In another embodiment, the registration between the frame and the head and brain can be achieved by performing imaging (for example MRI, CT, thomosynthesis, or x-ray) with the frame placed around the subject's head, allowing the transducer locations to be determined by imaging visible fiducial markers in the frame.

Although the preceding example embodiment involves the fabrication and use of a patient-specific frame that conforms to the anatomical curvature of the patient's head, it will be understood that this embodiment is included to provide one illustrative example of how the transcranial ultrasound transducer array elements may be supported.

According to another example implementation, the transcranial ultrasound transducer array elements may be supported by a support frame that does not have a patient specific shape, but is configured to support the plurality of transcranial ultrasound transducer array elements such that the transcranial ultrasound transducer array elements are adjustable. For example, the transcranial ultrasound transducer array elements may be manually or automatically adjustable relative to the support frame, in order to adjust the positions and orientations to match or approximate the positions and orientations calculated based on the volumetric image data associated with the patient. For example, the support frame may include one or more motors for varying the positions and/or orientations of the transcranial ultrasound transducer array elements. In some example implementations, the transducer may be held in place with rigid or flexible arms, holders, bands, or other suitable securing mechanisms.

In some example embodiments, one or more of the transcranial ultrasound transducer array elements may be configured to emit an energy beam toward the skull of the patient and to detect energy that is reflected from the skull in order to facilitate the detection of a local spatial offset of the skull of the patient relative to the patient-specific frame. The detected spatial offsets may then be employed to correct a spatial registration of the transducers relative to the skull in order to achieve a pre-selected focusing depth within or adjacent to the skull.

In some example implementations, the frequency of one or more transcranial ultrasound transducer array elements of the array may be determined (e.g. optimized) based on thickness and density of the adjacent skull bone. By incorporating these frequencies, the acoustic power at the focus may be increased (e.g. as shown in FIGS. 6A-F, and described in the Examples below), and this may result in improved performance compared to the case of using a conventional clinical hemispherical array.

In one example embodiment, the local speed of sound within the skull could be estimated, for example, based on the local skull thickness and composition as determined based on the volumetric image data, and using known tissue properties.

Figure 2C:
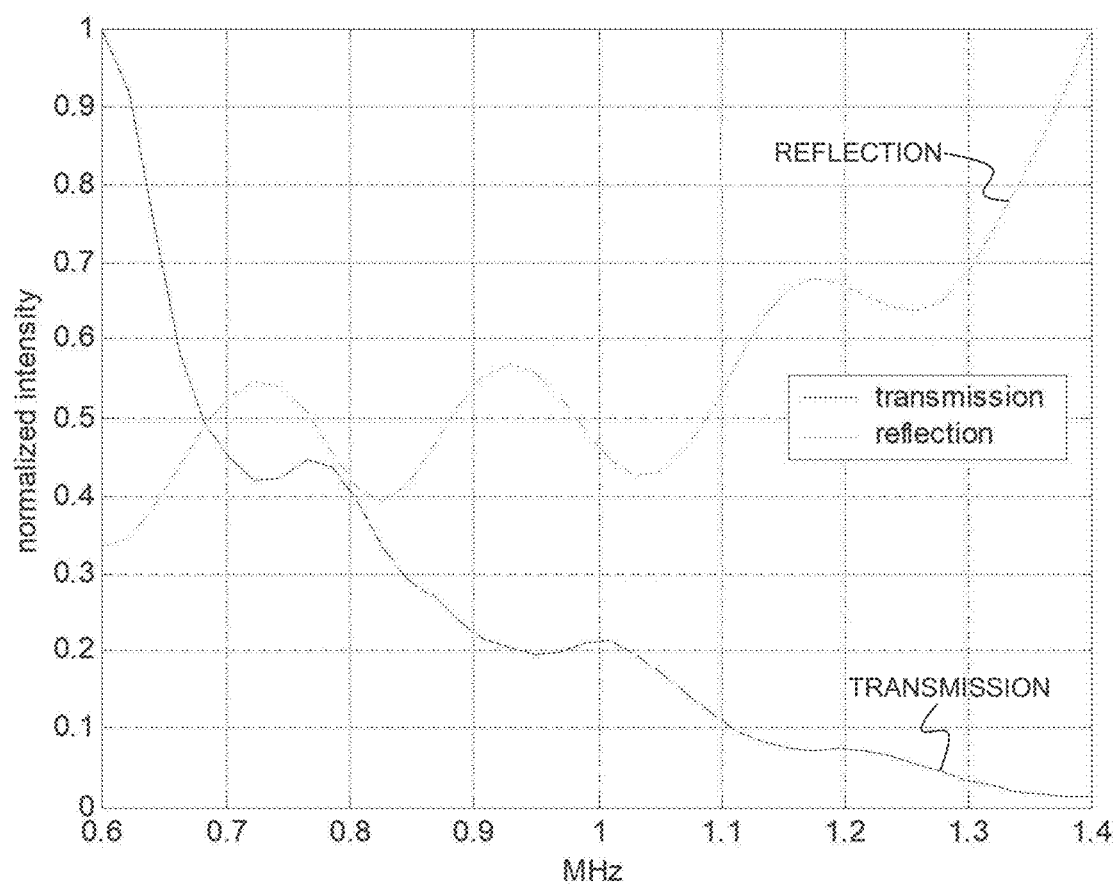
FIG. 2C plots normalized transmission and reflection spectra for a skull, showing the presence of resonant features that may be employed for the local determination of the speed of sound within the skull.

In another example implementation, the local speed of sound within the skull could be measured, for one or more transcranial ultrasound transducer array elements, by transmitting a wideband burst of ultrasound and capturing the reflected ultrasound wave. The reflected ultrasound wave could then be spectrally analyzed to determine the local thickness and speed of sound. Alternatively, instead of using a wideband burst, spectral measurements could be made by transmitting a series of narrowband ultrasound waves, each having a different frequency, such that the frequencies span a suitable frequency range. Such wideband or serial narrowband measurements provide an acoustic spectrum, which may be processed to identify the thickness resonances of the skull. The thickness of the skull produces resonances in which the reflected waves are in phase with the entering wave, causing minimum reflections. The spectrum shows also peaks when the waves are out of phase indicating minimum transmission. Examples of such resonant features are shown in FIG. 2C. Since the resonant frequency of the bone layer is $$f_r = \frac{nc_b}{2d},$$

where n is integer=1, 2, 3, . . . and $c_b$ is the average speed of sound in the bone and d is the skull thickness, these resonances may be employed to determine the local speed of sound, by obtaining the local skull thickness from the pre-operative (e.g. CT or MRI) volumetric image data and solving for the local speed of sound. This local speed of sound can then be advantageously employed to determine (correct, fine tune) the phase or timing delays of the various transcranial ultrasound transducer array elements for far-field focusing.

Additionally or alternatively, the local skull thickness and speed of sound may be employed to select a suitable operating frequency for each transcranial ultrasound transducer array element in order to achieve an increased or maximum local transmission. The use of frequency-tuned transcranial ultrasound transducer array elements could provide a significant pressure gain for burst transmissions.

Figure 3:
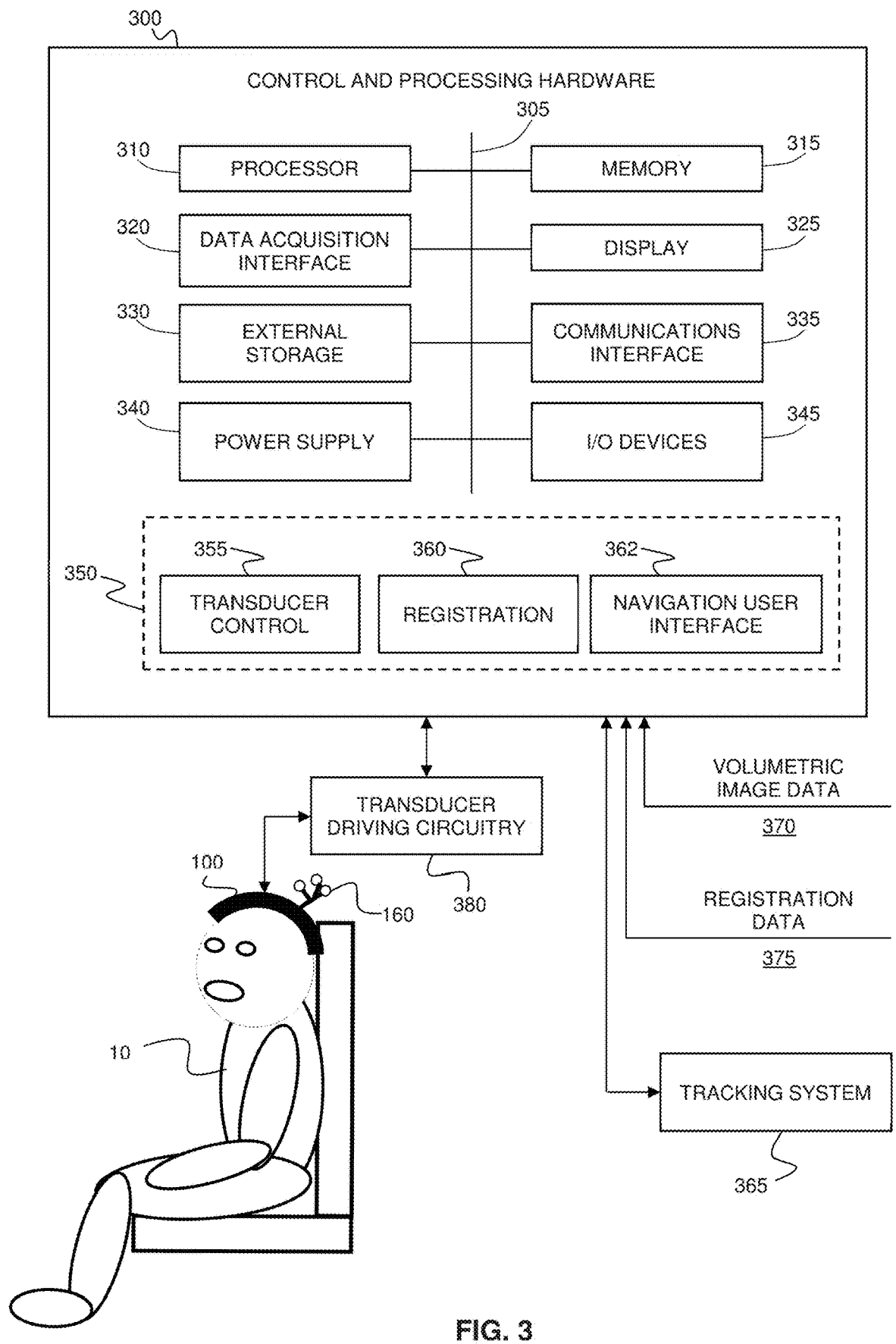
FIG. 3 shows a system for performing transcranial diagnostic and/or therapeutic procedures.

FIG. 3 provides a block diagram illustrating an example implementation of a system for performing diagnostic or therapeutic transcranial procedures. Control and processing hardware 300 is operably connected to the transcranial headset 100, optionally via transducer driver electronics/circuitry 380.

The control and processing hardware 300, which includes one or more processors 310 (for example, a CPU/microprocessor), bus 305, memory 315, which may include random access memory (RAM) and/or read only memory (ROM), a data acquisition interface 320, a display 325, external storage 330, one more communications interfaces 335, a power supply 340, and one or more input/output devices and/or interfaces 345 (e.g. a speaker, a user input device, such as a keyboard, a keypad, a mouse, a position tracked stylus, a position tracked probe, a foot switch, and/or a microphone for capturing speech commands).

Volumetric image data 370 and transducer registration data 375 may be stored on an external database or stored in memory 315 or storage 330 of control and processing hardware 300.

The tracking system 365 may optionally be employed to track the position and orientation of the patient, via detection of one or more fiducial markers 160 attached to the transcranial headset 100, and optionally one or more medical instruments or devices also having fiducial markers attached thereto. For example, passive or active signals emitted from the fiducial markers may be detected by a stereographic tracking system employing two tracking cameras. The transducer driving electronics/circuitry 380 may include, for example, but is not limited to, Tx/Rx switches, transmit and/or receive beamformers.

The control and processing hardware 300 may be programmed with programs, subroutines, applications or modules 350, which include executable instructions, which when executed by the one or more processors 310, causes the system to perform one or more methods described in the present disclosure. Such instructions may be stored, for example, in memory 315 and/or other storage.

In the example embodiment shown, the transducer control module 355 includes executable instructions for controlling the transducers of the transcranial headset 100 to deliver energy to a target location or region of interest, based on the registration of the transducer positions and orientations with the volumetric image data as per the transducer registration data 375. For example, the transcranial headset 100 may support a plurality of phased-array transducers, and transducer control module 355 may control the beamforming applied (on transmit and/or receive) to deliver, based on the known positions and orientations of the phased array transducers relative to the volumetric image data, one or more focused energy beams to a region of interest in the far field regions of the transcranial ultrasound transducer array elements. The region of interest may be specified intraoperatively by a user (e.g. via a user interface controlled by control and processing hardware 300) or according to a pre-established surgical plan.

The registration module 360 may optionally be employed for registering volumetric image data 370 to an intraoperative reference frame associated with tracking system 365. The optional guidance user interface module 362 includes executable instructions for displaying a user interface showing spatially registered volumetric images for image-guided procedures. The registration module 360 may also intraoperatively receive spatial correction information based on a detected spatial offset between the transcranial frame and the patient's head (which, as described above, may be provided by a subset of distance-sensing transducers) and employ this spatial correction information to dynamically adjust (e.g. correct) the registration between the transducers and the volumetric image data.

Although only one of each component is illustrated in FIG. 3, any number of each component can be included in the control and processing hardware 300. For example, a computer typically contains a number of different data storage media. Furthermore, although bus 305 is depicted as a single connection between all of the components, it will be appreciated that the bus 305 may represent one or more circuits, devices or communication channels which link two or more of the components. For example, in personal computers, bus 305 often includes or is a motherboard. Control and processing hardware 300 may include many more or less components than those shown.

The control and processing hardware 300 may be implemented as one or more physical devices that are coupled to processor 310 through one of more communications channels or interfaces. For example, control and processing hardware 300 can be implemented using application specific integrated circuits (ASICs). Alternatively, control and processing hardware 300 can be implemented as a combination of hardware and software, where the software is loaded into the processor from the memory or over a network connection.

Some aspects of the present disclosure can be embodied, at least in part, in software, which, when executed on a computing system, transforms a computing system into a specialty-purpose computing system that is capable of performing the methods disclosed herein. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

While the example embodiments described above and in the following examples illustrate transcranial ultrasound transducer array configurations in which the transcranial ultrasound transducer array elements are focused within the skull, it will be understood that while intra-skull focusing may be beneficial in some implementations, other implementations may employ focusing configurations in which one or more of the transcranial ultrasound transducer array elements have a respective focal point that lies outside of, and adjacent to, the skull (e.g. adjacent to the inner or outer skull surfaces), such that the ultrasound beams that extends within the brain overlap in the far-field region.

Although some of the example embodiments described herein illustrate transcranial ultrasound transducer arrays having array elements with equal focal lengths, it will be understood that the focal lengths may differ among transcranial ultrasound transducer array elements, for example, in order to account for local variations in the skull thickness and/or shape. Furthermore, the sizes, spatial offsets relative to the skull, and/or F number of the transcranial ultrasound transducer array elements may vary among elements.

In some example embodiments, the transcranial ultrasound transducer array elements are configured and spatially arranged such that the far fields of each of the ultrasound beams overlap within a spatial region within the brain that permits the selection of a focusing target within an extended focusing region, such as the extended region shown in FIG. 1A. In other example embodiments, the transcranial ultrasound transducer array elements are configured and spatially arranged such that spatial overlap of the far field regions of the ultrasound beams occurs within a spatial region that includes a pre-selected target. In other words, the spatial configuration of the transcranial ultrasound transducer array elements may be selected based on a known target location within the brain.

Many of the example embodiments of the present disclosure pertain to the use of pulsed excitation and the control of the time delay (or phase) of the pulses from the transcranial ultrasound transducer array elements. However, although pulsed excitation may be beneficial in achieving a sharp focus, particularly for focal regions away from the natural focus of the transcranial ultrasound transducer array, continuous wave excitation of the transcranial ultrasound transducer array elements, with appropriate phase control, may also be achieved in order to produce a focal region in the far field.

In some example embodiments, the transcranial ultrasound transducer array may be operated at two or more frequencies, such that different subsets of the transcranial ultrasound transducer array elements operate at different frequencies. For example, dual frequency excitation has shown promise in preclinical work to date in enhancing acoustic cavitation. As demonstrated in the examples provided below, tight focusing and dual-frequency excitation are also achievable according the present embodiments that employ far field focusing.

As shown in the examples provided below, the present example embodiments may be employed to generate high acoustic pressures at off-center targets, using fewer ultrasound elements than conventional transcranial ultrasound array devices. The example embodiments disclosed herein, and variations or adaptations thereof, may be employed for a wide variety of transcranial procedures, including, but not limited to, neuromodulation, neurostimulation, neuroimaging, neuro-monitoring, focused-ultrasound transcranial ablation, mild heating (hyperthermia), mechanical excitation of the brain for diagnostic or therapeutic purposes, manipulation, control, excitation or sensing of gas bubbles, liquid droplets, solid particles, cells, nanoparticles, quantum dots or electronic circuits or devices, focused-ultrasound transcranial excitation or sensing of brain implants, devices, electronic circuits or sensors and transcranial procedures involving the use of focused ultrasound to disruption and opening of the blood-brain barrier for delivery of therapeutic or diagnostic agents, cells, particles, droplets, bubbles, electronic devices, transmitters, sensors or other foreign material for diagnostic or therapeutic purposes.

It will be understood that although the present disclosure includes many example embodiments pertaining to a transcranial ultrasound transducer array that is to be placed around the patient's head, the systems, devices and method disclosed herein may be adapted to provide a transcranial apparatus for performing diagnostic or therapeutic procedures on other parts or portions of the body. The support frame to support transducers for the far field focusing may be fabricated according to volumetric image data of other body regions or body portions. For example, a support frame may be fabricated, based on volumetric image data of a patient's knee, such that the support frame conforms to the contour of the patient's knee, for performing a diagnostic or therapeutic procedure on the knee using the transducer supported by the support frame. Similarly, a support frame may be fabricated, based on volumetric image data of a patient's spine, such that the support frame conforms to the contour of the patient's spine, for performing a diagnostic or therapeutic procedure on the spine using the transducer supported by the support frame.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Patient Imaging Data

A CT scan (LightSpeed VCT, GE Healthcare, Chalfont St Giles, UK) of a human head can be obtained and used in each of the numerical simulations. The CT dataset (512×512×328 voxels with uniform voxels of size 625×625×625 mm$^3$) can be used to extract density and morphology information. The density is obtained using a linear relation with the Hounsfield Units, using knowledge of the densities of brain tissue and air in the CT scan. The skull CT data is then segmented and interpolated such that the discretization in the numerical simulations is $\lambda$=10, where $\lambda$ is the wavelength of the ultrasound in water. In the case of multi-frequency numerical simulations, the discretization is taken as $\lambda$=10 at the highest frequency.

Example 2: Patient Treatment Modeling

1) Acoustic Simulations

A hybrid numerical model is employed to perform simulations involving the propagation of ultrasound bursts of variable length emitted from the transcranial ultrasound transducer array elements. The numerical method combines finite difference simulations with the grid method. This hybrid model calculates the pressure field in the brain and the particle displacement field in the cranial bone using finite difference methods, while coupling these different equations on the boundary using the grid method. The governing equation of acoustic propagation in fluids is given by:

$$(\partial_{tt}^2 + 2\alpha_L c \partial_t) p = c^2 \left( \nabla^2 - \frac{1}{\rho} \nabla \rho \cdot \nabla \right) p, \qquad (1)$$

where p denotes the acoustic pressure, $\alpha_L$ is the longitudinal attenuation coefficient, c is the speed of sound, and $\rho$ is the density. In solid domains, the governing equation is given by:

$$\rho \partial_{tt}^2 u = (\mu + \eta \partial_t) \nabla^2 u + \left( \lambda + \mu + \xi \partial_t + \frac{\eta}{3} \partial_t \right) \nabla (\nabla \cdot u), \qquad (2)$$

where u is the vector field of the particle displacements in the three Cartesian directions, $\lambda$ and $\mu$ are the first and second Lamé coefficients, and $\eta$ and $\xi$ are the first and second viscosity parameters. Details of the numerical implementation of equations 1 and 2 are given in the Appendix of Pulkkinen et al. (A. Pulkkinen, B. Werner, E. Martin, and K. Hynynen, "Numerical simulations of clinical focused ultrasound functional neurosurgery." Physics in medicine and biology, vol. 59, no. 7, pp. 1679-700, 2014). The longitudinal speed of sound, $c_L$, and attenuation, $\alpha_L$, in skull, were found using a spline interpolation [30]. Since the present inventors are unaware of any experimental shear speed and attenuation data as a function of density, scaling factors are used, so that $$c_s = \frac{1400}{2700} c_L(\rho) \text{ and } \alpha_s = \frac{90}{85} \alpha_L(\rho). \qquad [15]$$

Time steps and spatial voxel sizes are frequency-dependent, such that the spatial voxel size is of size $\lambda$/10, and a maximum Courant-Friedrichs-Lewy (CFL) value of 0.1 is obtained. The CFL is calculated as CFL=c$\Delta$t$\Delta$h$^{-1}$, for spatial discretization step size $\Delta$h and temporal step size $\Delta$t, where the CFL is calculated in each domain separately and for both longitudinal and shear sound speeds in bone.

The Neumann boundary condition, defined as $$\partial_n p = g, \qquad (3)$$

is used on interfaces between transducer faces and coupling liquid, where n is the normal to the transducer surface, $\rho$ is the pressure, and g is a term describing the prescribed oscillation of the transducer surfaces. The absorbing boundary condition is used on other boundaries.

A Fast Fourier Transform of the peak cycle of the acoustic field is taken to obtain the time-averaged pressure field over the treatment domain. The total size of the treatment domain varies as a function of frequency, from 250 kHz to 1 MHz. Each simulation is run over a sufficient number of temporal steps to allow the simulation of the propagation of ultrasound 30 cm in water.

The phasing of each transcranial ultrasound transducer array element is obtained by first sending a pulse from the target focus in the skull, and delaying the transmission pulse based on the time-of-flight obtained to each transcranial ultrasound transducer array element. In this way, the peak of the Gaussian-enveloped sinusoid is synced among all the transcranial ultrasound transducer array elements. Each sonicating transducer element is then driven with the time-delayed Gaussian-enveloped sinusoidal signal obtained from the reversed problem.

2) Thermal Simulations

From the particle displacement field in bone, the absorbed power density is calculated, using the relation $$Q = -\frac{\omega}{2} \Im(\sigma_i \bar{\varepsilon}_i), \qquad (4)$$

where $\omega$ is the angular frequency, $\sigma$ denotes the stress tensor, $\varepsilon$ denotes the strain tensor, and $\Im$ denotes the imaginary component. The absorbed power density in the entire domain is then used as a time-independent heat source in the Pennes bioheat equation, defined as:

$$\rho C_t \partial_t T = \kappa \nabla^2 T + Q, \qquad (5)$$

where ρ is the skull density, C is the specific heat capacity in the skull, κ is the skull thermal conductivity, and Q is a constant heat source. Equation (5) is solved using a finite difference time domain (FDTD) technique. FIG. 4 summarizes the parameters employed when performing simulations of acoustic and thermal fields.

A computer cluster consisting of eight Intel Xeon processors is used to perform the simulation of the finite-difference-grid simulations, while a standard desktop computer was used to analyze and process the data.

Example 3: Analysis of Focusing

FIGS. 5A-B compare a concave transducer focused inside the skull (FIG. with a flat λ/2 radius element (FIG. 5B) to illustrate the efficacy of focusing inside the skull. Both transducer powers are normalized to the same value, and the pressure fields are normalized to the maximum pressure in the focused transducer case. It is noted that a logarithmic scale is employed to plot the acoustic pressure fields. Both transducers are positioned normal to the skull surface. The figures illustrate a schematic of the geometry through the coronal plane, with the arrows pointing to the position of the transverse plane through which the pressure maps are displayed. It is clear in this example that the curved (focused) transducer transmits a higher intensity acoustic field through the skull, with a more disperse acoustic field than the flat transducer of size λ/2.

Figure 5C:
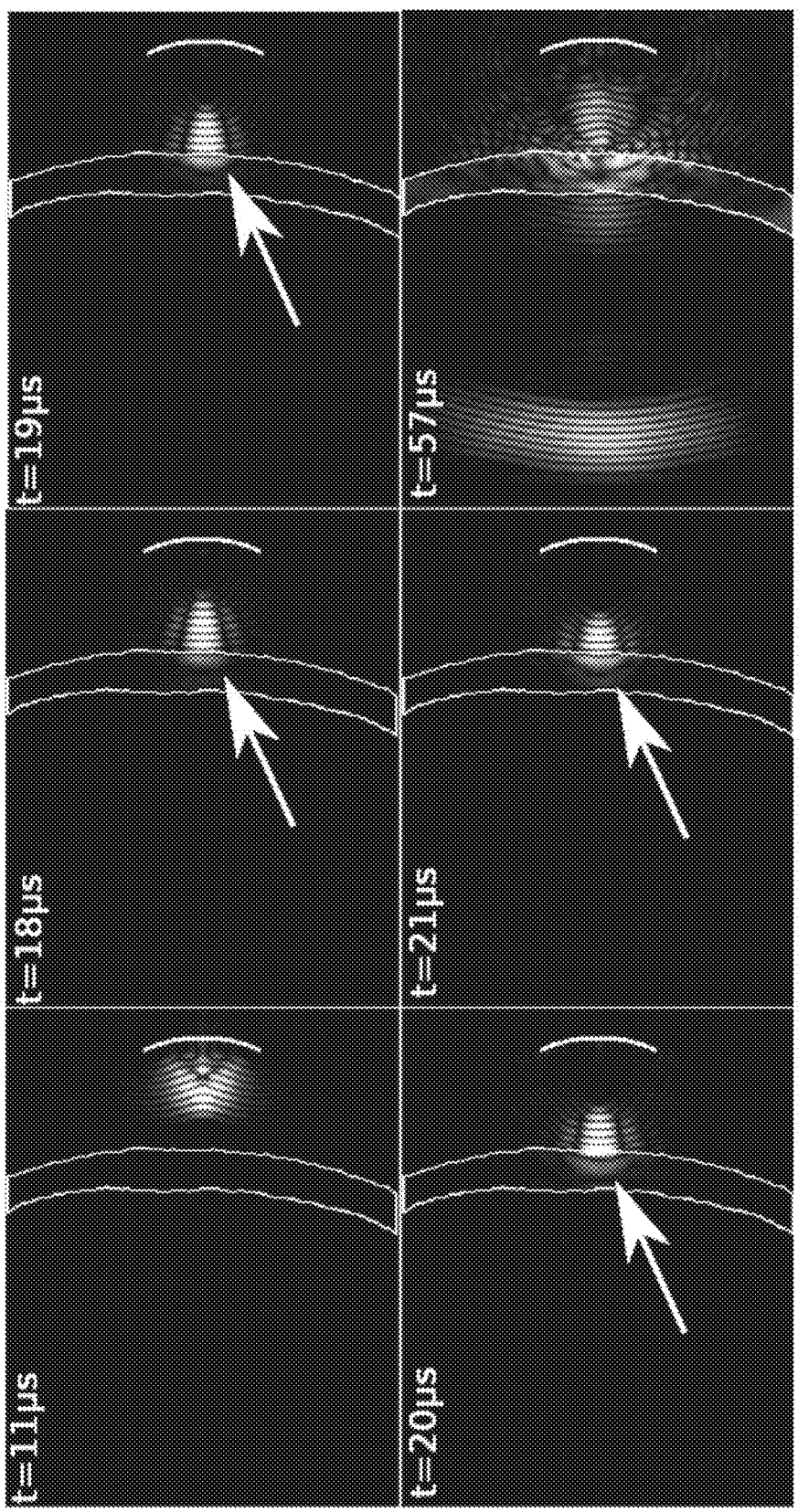
FIG. 5C illustrates the temporal wave propagation of a 5-cycle pulse emitted from a single transducer focused inside the skull, at 11, 18, 19, 20, 21, and 57 μs.

FIG. 5C presents a montage illustrating the concept of focusing the ultrasonic wave through the skull at timepoints of 11, 18, 19, 20, 21, and 57 μs. The transducer (f-number=1) is focused inside the skull, and is placed 20 mm away from the skull surface. This figure demonstrates the conversion of a convergent spherical wave to a plane wave, to a divergent spherical wave, to minimize transmission losses at the skull. At 18 μs, the spherical wave is converted into a planar wave which propagates at normal incidence through the skull, as shown at t=18; 19; 20, and 21 μs. At 57 μs, the attenuated wave is shown inside the head as a diverging spherical wave.

Figure 6A:
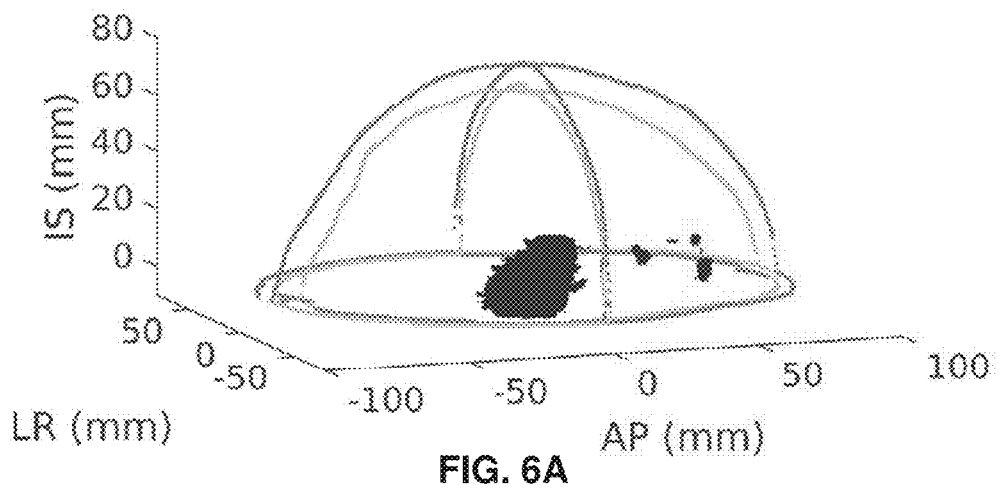
FIGS. 6A-C show a comparison of the focusing capability of a 64-element array for the different array configurations of: (A) a non-conformal hemisphere, (B) a conformal arrangement of flat array elements, and (C) a conformal arrangement of focused transducer elements.
Figure 6B:
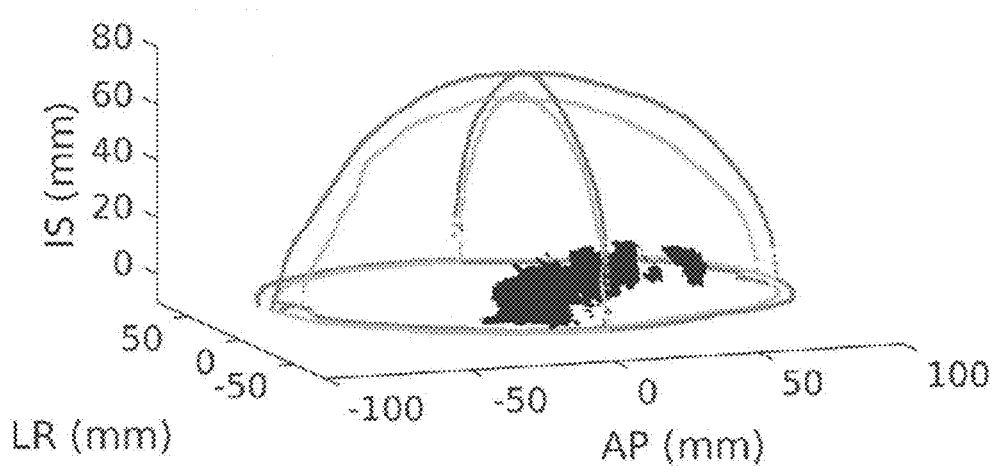
Figure 6C:
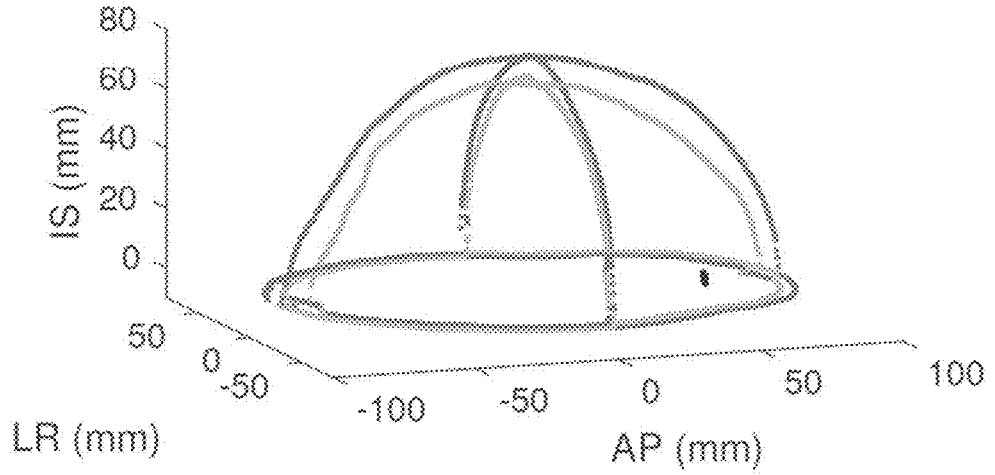

FIGS. 6A-C illustrate the need for focused ultrasound transducers in a pattern conformal to the skull surface. The figures show −3 dB isosurfaces for 64-element arrays configured as: (A) a non-conformal hemisphere, (B) a conformal arrangement of flat array elements, and (C) a conformal arrangement of focused transducer elements. In these three examples, it is clear that the focusing of the beam 6 cm anterior to the center of the skull is made possible with the conformal array consisting of transducer elements focused inside the skull.

Figure 6D:
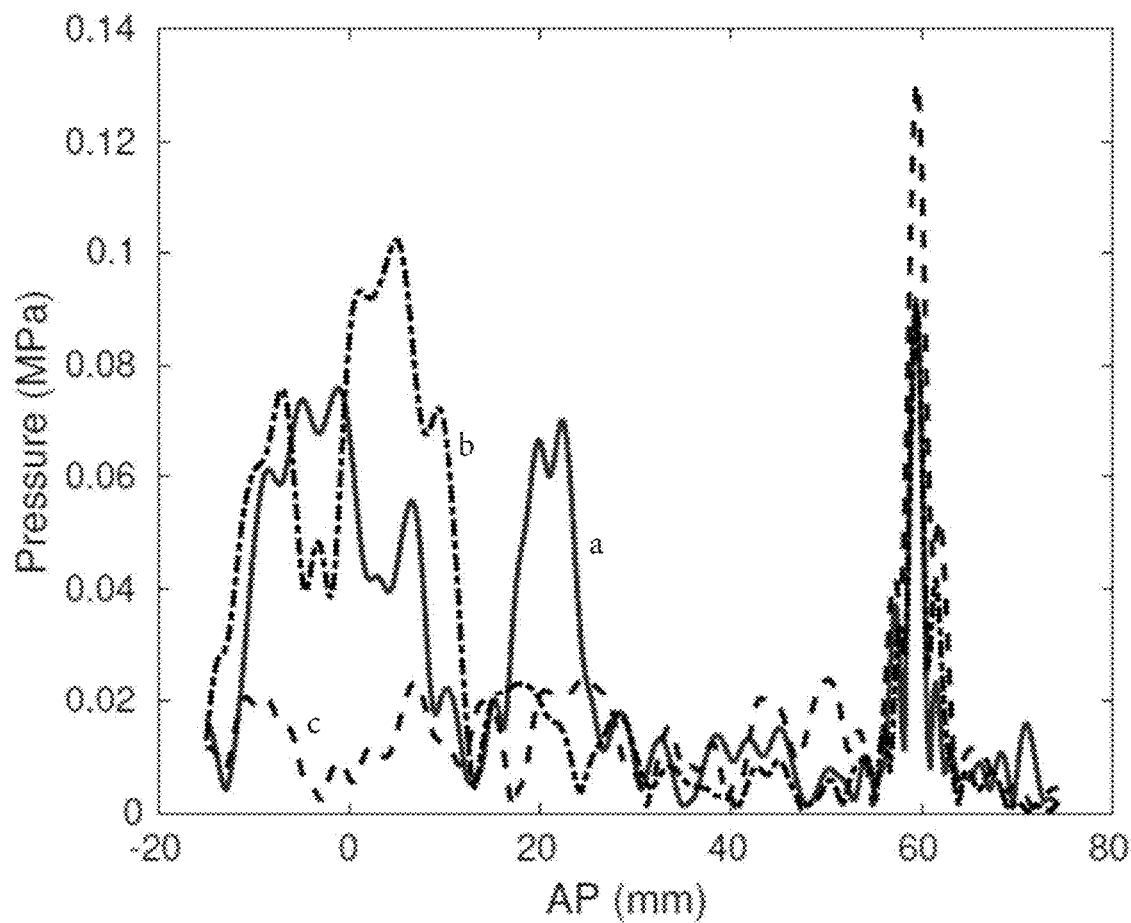
FIG. 6D plots the pressure through the focus in the anterior-posterior (AP) direction for the different array configurations of: a non-conformal hemisphere (solid), conformal arrangement of flat array elements (short dash), and conformal arrangement of focused transducer elements (long dash).

This is further illustrated in FIG. 6D, where the pressure through the focus along the anterior-posterior (AP) direction is illustrated for the different array configurations: non-conformal hemisphere (solid), conformal arrangement of flat array elements (short dash), and conformal arrangement of focused transducer elements (long dash). It is clear from this figure that the conformal focused array (long dash) provides the optimal focus.

Figure 6E:
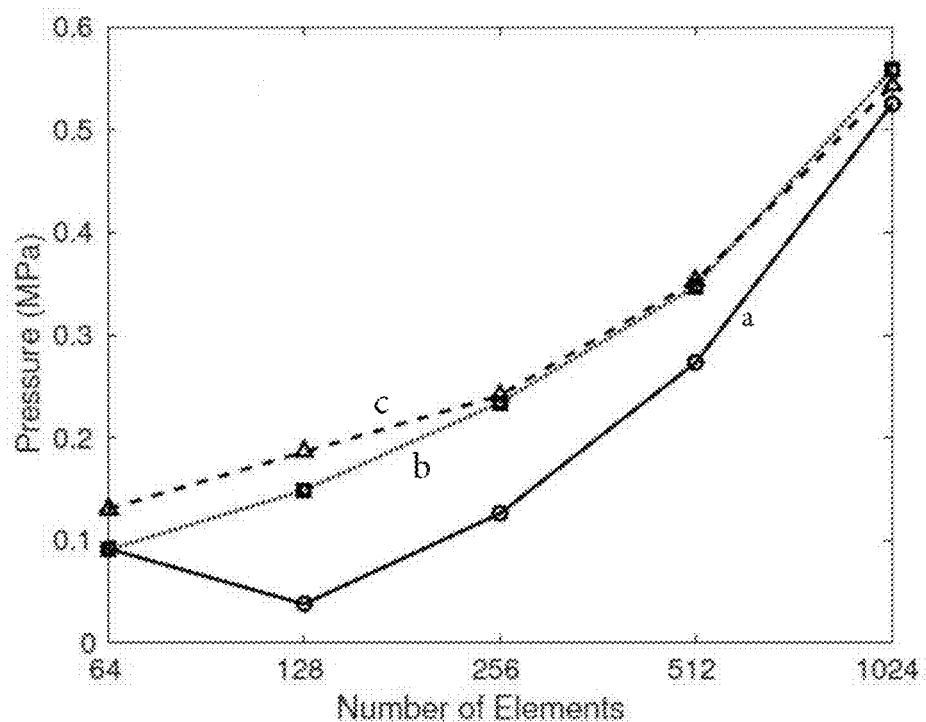
FIG. 6E plots the dependence of pressure (through the focus in the anterior-posterior (AP) direction) on the number of transducer elements for the different array configurations of: a non-conformal hemisphere (solid), conformal arrangement of flat array elements (short dash), and conformal arrangement of focused transducer elements (long dash).
Figure 6F:
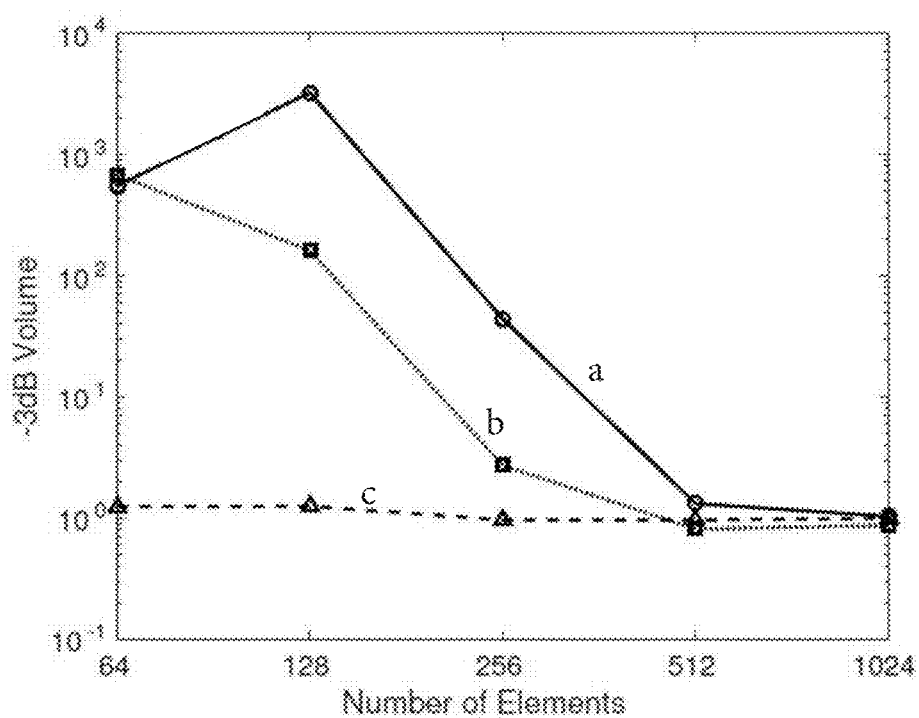
FIG. 6F plots the dependence of the −3 dB volume (through the focus in the anterior-posterior (AP) direction) on the number of transducer elements for the different array configurations of: a non-conformal hemisphere (solid), conformal arrangement of flat array elements (short dash), and conformal arrangement of focused transducer elements (long dash).

Referring now to FIGS. 6E and 6F, the dependence of the peak focal pressure on the number of transducer elements in the array, and the dependence of the −3 dB volume on the number of transducer elements in the array, are respectively illustrated, for focusing in the anterior-posterior (AP) direction. The plotted curves show results the different array configurations of: a non-conformal hemisphere (solid), conformal arrangement of flat array elements (short dash), and conformal arrangement of focused transducer elements (long dash). It is noted that the vertical axis of FIG. 12B is shown on a logarithmic scale. Although the peak pressure at the focus increases as a function of the number of elements, as expected, for a focused conformal array the −3 dB volume within the brain is relatively constant as a function of the number of elements. This is in contrast to the conventional hemispherical array and the array consisting of flat elements, where the −3 dB volume decreases as a function of the number of elements.

As shown in both FIGS. 6E and 6F, the difference between the different array designs becomes indistinguishable as the number of elements in the array increases. That is, the difference in peak pressure and −3 dB volume become very similar for all three array designs. This is a result of the array configurations becoming more similar as more elements are added. Where the number of elements increases, the f-number of the curved elements in the focused array naturally decreases, and therefore converges on the flat array. This is because the minimum distance to the middle of the skull remains fixed, while the maximum diameter of each element must become smaller. In the case of a full array, the maximum permissible transducer diameter decreases as the number of elements remains fixed and the transducer array surface area becomes smaller, as in the case of a conformal array of transducers focused at the skull surface. Although the directivity of each transducer is small, as the number of elements increases, each element in the conformal array more closely approximates the forward propagation of the ultrasonic field from a single element in the full array.

Figure 7A:
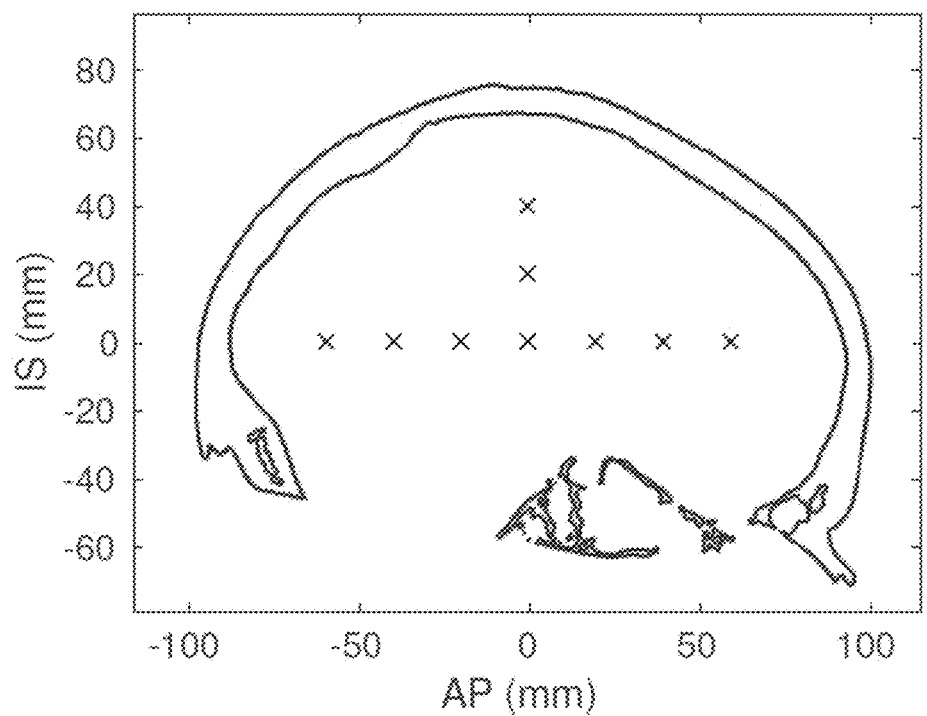
FIGS. 7A-B show the locations of the target foci in the (A) sagittal and (B) coronal planes.
Figure 7B:
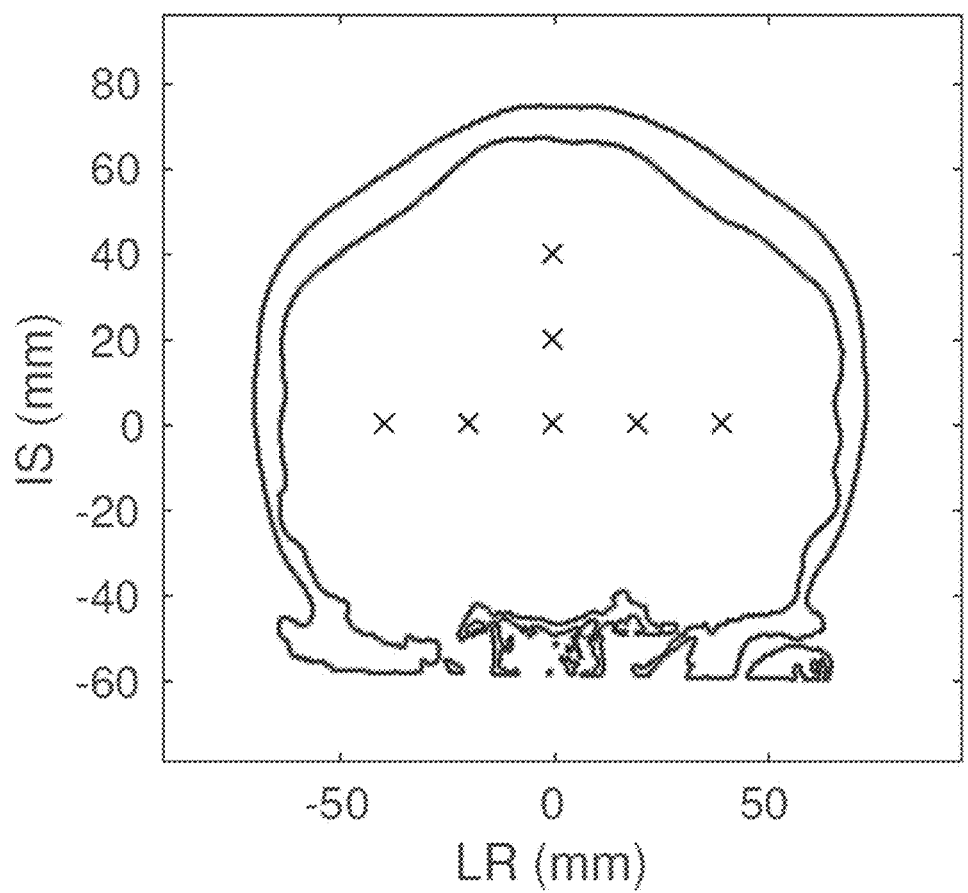
Figure 8A:
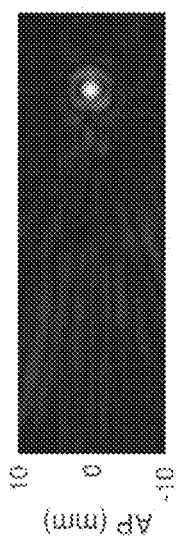
FIGS. 8A-I plot the acoustic pressure maps in the axial, coronal, and sagittal planes for steered positions at 0 mm, 20 mm and 40 mm.
Figure 8B:
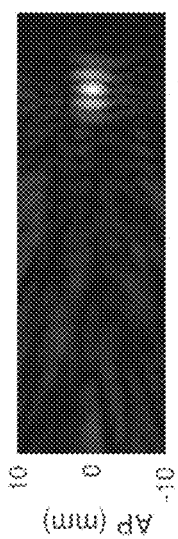
Figure 8C:
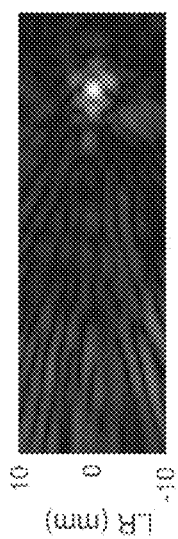
Figure 8D:
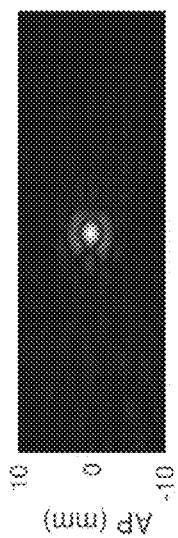
Figure 8E:
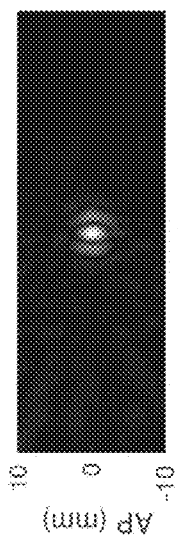
Figure 8F:
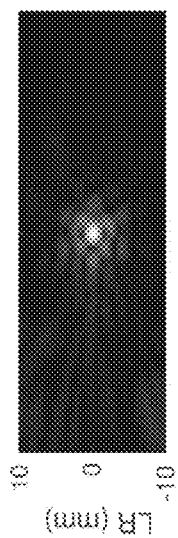
Figure 8G:
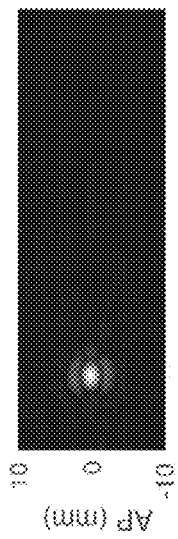
Figure 8H:
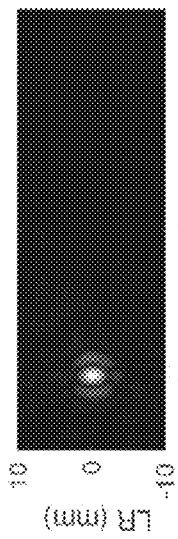
Figure 8I:
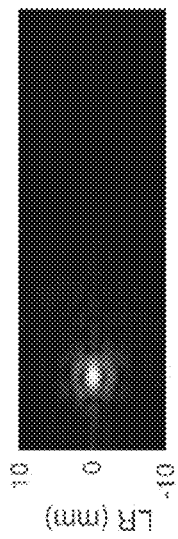

To analyze the focusing quality of each configuration of the phased array, the acoustic field was steered to different targets spanning the spatial extent of the brain. FIGS. 7A-B illustrate the locations of the target foci in the cranium in both the sagittal and coronal planes. The −3 dB main lobe beamwidth was analyzed for foci in the anterior-posterior (AP), left-right (LR) and inferior-superior (IS) directions. In addition, the peak sidelobe ratio was used to determine the spread of the focus. Finally, the peak focal pressure was analyzed.

FIGS. 8A-I illustrates the simulated normalized acoustic pressure fields when steering in the left-right (LR) (a-c), the anterior-posterior (AP) (d-f), and the inferior-superior (IS) (g-i) directions. The example transducer array simulated in this example consisted of 256 elements, and was sonicated at 500 kHz, with a pulse length of 3 cycles. A mild degradation of focal quality is observed when steering laterally (f) and superior to the center of the skull cavity(i).

Figure 9A:
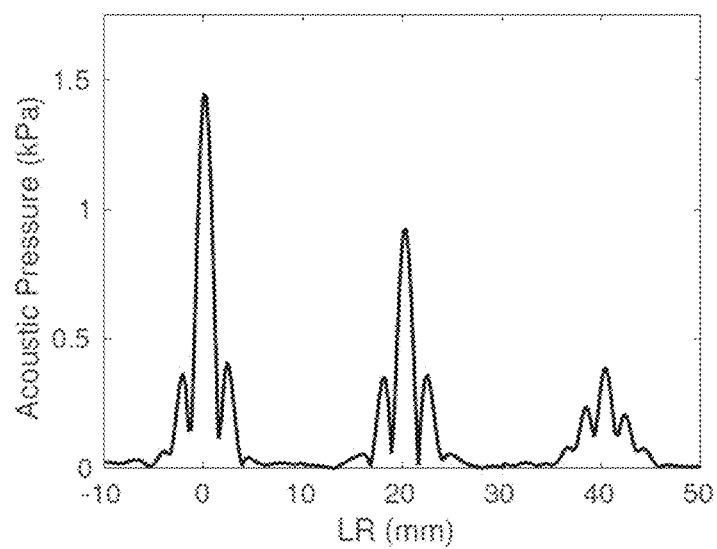
FIG. 9A-C plot the demonstration of the effect of electronically steering the phased array in the AP, LR, and IS directions, for positions through the focus along the axial, coronal, and sagittal planes for the geometric focus, as well as steering 20 and 40 mm from the geometric focus in the LR (A) and IS (C) directions, as well as steering 20, 40, and 60 mm from the geometric focus in the AP (B) direction.
Figure 9B:
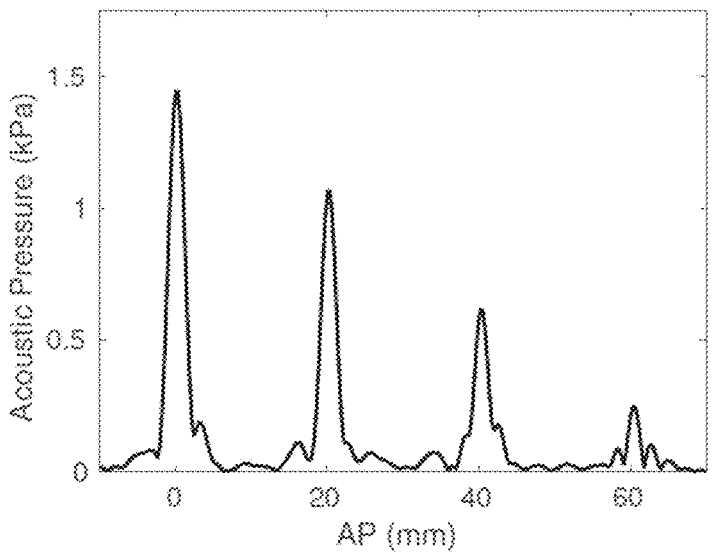
Figure 9C:
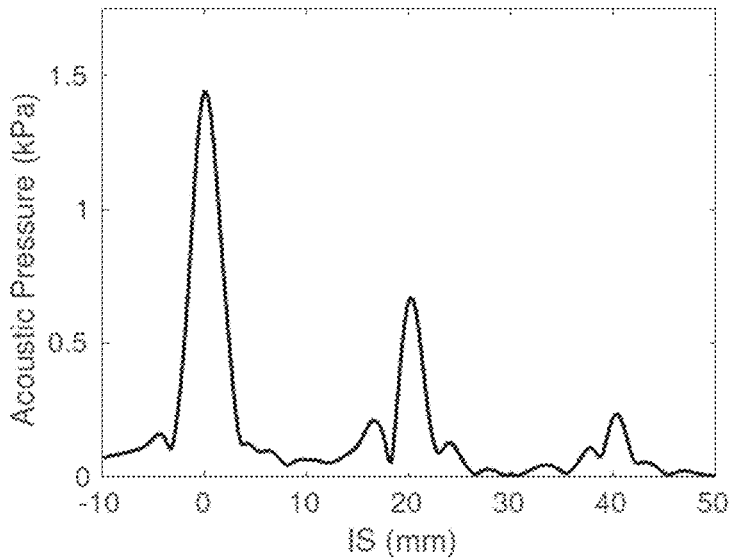

FIGS. 9A-C supplement the results presented in FIGS. 8A-I by providing results demonstrating the steering performance of the phased array design for positions through the focus along the axial, coronal, and sagittal planes for the center of the skull cavity, as well as steering 20 and 40 mm from the center of the skull cavity in the LR (a) and IS (c) directions, as well as steering 20, 40, and 60 mm from the center of the skull cavity in the AP (b) direction. These figures highlight the relative amplitude of the sidelobes to the mainlobes increasing as one steers away from the center of the skull cavity in all three directions, as well as a decrease in the peak pressure amplitude.

Figure 10A:
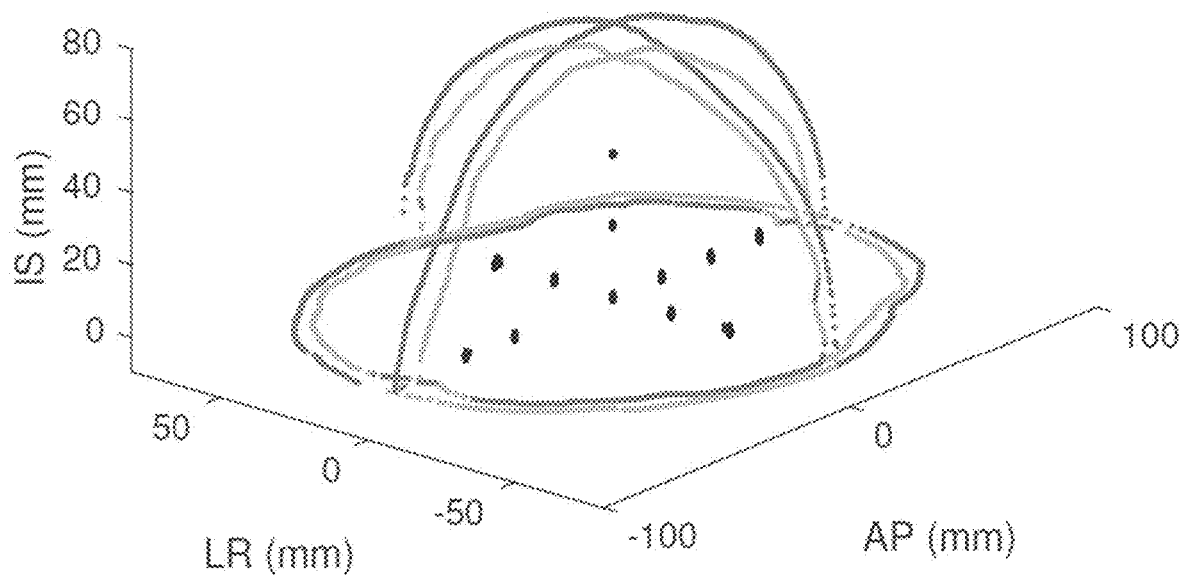
FIGS. 10A-B plot the (A) −3 dB and (B) −6 dB isosurfaces illustrating the quality of trans-skull focusing at 500 kHz.
Figure 10B:
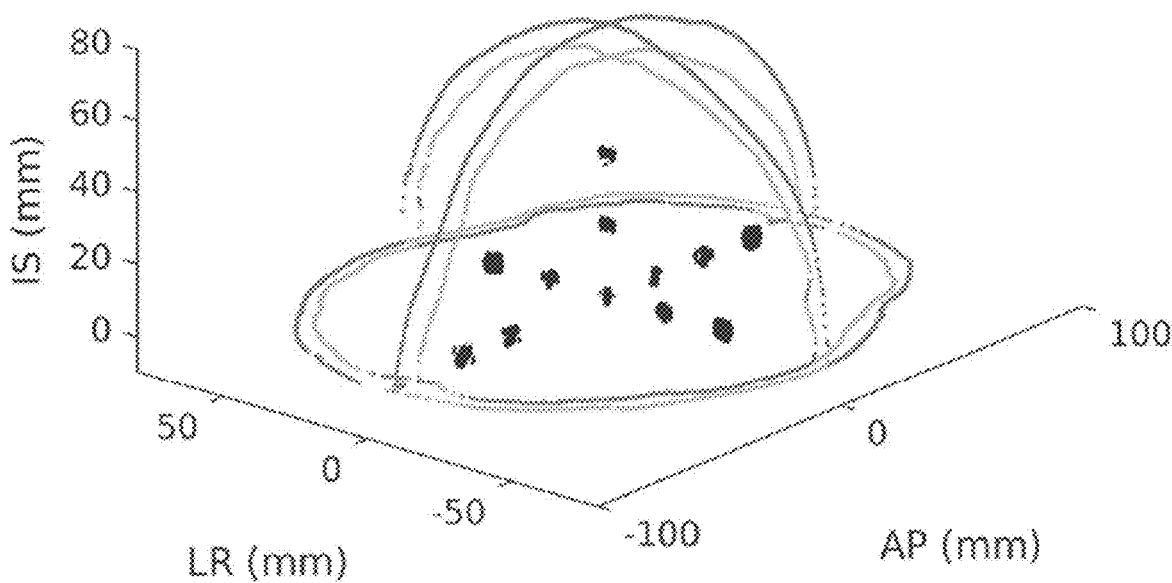

FIGS. 10A-B illustrate the simulated (a) −3 dB and (b) −6 dB isosurfaces at the steered locations throughout the skull cavity with a 256-element phased array sonicating at 500 kHz. The light gray line shown in each figure is the inner surface of the skull, and the dark gray line is the outer surface. From this figure, it is apparent that there are pronounced −6 dB sidelobes while sonicating far from the of the array.

Example 4: Variable Transducer Configurations

The configuration of the transducer elements of the array is dependent on a number of factors. Firstly, since the transducers are relatively close to the patient's head (on the order of millimeters from the skin surface), the total number of elements is limited significantly by the limited surface area of the array, as compared to the more traditional hemispherical array of transducer elements. Secondly, the focusing depth and distance to the skull surface dictate the radius of curvature of each fixed focus transducer (but not phased array). Finally, the combination of the first two effects, whereby two transducers of equal focusing depths and different size have different areas, will then have different f-numbers and the far-field acoustic field will hence be quite different. Each of these factors affect the steering range and the acoustic output of the transcranial transducer array.

In the present example simulations, the transducer array geometry was generated by maintaining a fixed number of transducers in the array. Once the number of transcranial array transducers elements was determined, the positions were assigned using Vogel's method, such that the placement was optimally random and spaced out as far as possible given N. Given these fixed distances, the maximum transducer area was determined, with consideration being given to engineering limitations of inter-element spacing, such that a reasonable gap was left. All transducers in each array were of the same size. The configurations are summarized in table shown in FIG. 11A. As explained above, this method of determining a spatial arrangement of transducers of the transcranial array is provided as a non-limiting example method, and other methods of determining the transducer array configuration may alternatively be employed.

In the present example simulations, after having determined an initial spatial arrangement of the transducer array elements, the incidence angle to the skull surface at the closest point to the transducer center was determined, and each transducer was rotated independently, such that the transducer was of normal incidence to the skull surface. Each transducer was then shifted towards or away from the skull surface in order to achieve equal distances from either the outer, inner, or midpoint of the skull, depending on the case at hand. The fixed distance from the skull was based on trial and error to determine the closest reasonable position of the transcranial ultrasound transducer array elements to the skull. This minimum distance was found to vary depending on both the total number of transducers in the array and the concavity of each transducer. In this way, all transcranial ultrasound transducer array elements were set normal to the skull surface and equidistant to the skull focus point. As explained above, such a configuration, involving equivalent focal depths within the skull for all transducer elements, provides one non-limiting example array configuration, and that other array configurations may depart from this equivalent-focus configuration while still being effective.

In one example simulation, the focusing depth of the transcranial ultrasound transducer elements were varied to determine the optimal focusing depth for peak transmission and focusing quality for a far-field intracranial focused location of y=60 mm. Three different focusing depths were tested: focusing at the outer surface, the inner surface, and in the middle of the skull. The chosen focusing depth affected the maximum permissible focal length and resultant f-number. FIG. 11B provides a table illustrating the result of focusing at the outer-, inner-, and mid-skull to steer to y=60 mm. By focusing at the inner- and mid-skull, one obtains a higher acoustic pressure than when focusing at the outer-skull. Meanwhile, the focusing quality significantly decreases when focusing at the inner-skull as compared to the mid- and outer-skull, as demonstrated by the increased −6 dB volume of heating. As such, in all subsequent simulations, each transducer is focused to the middle of the skull, in order to compromise between the ultrasound transmission and the focusing quality.

Figure 12A:
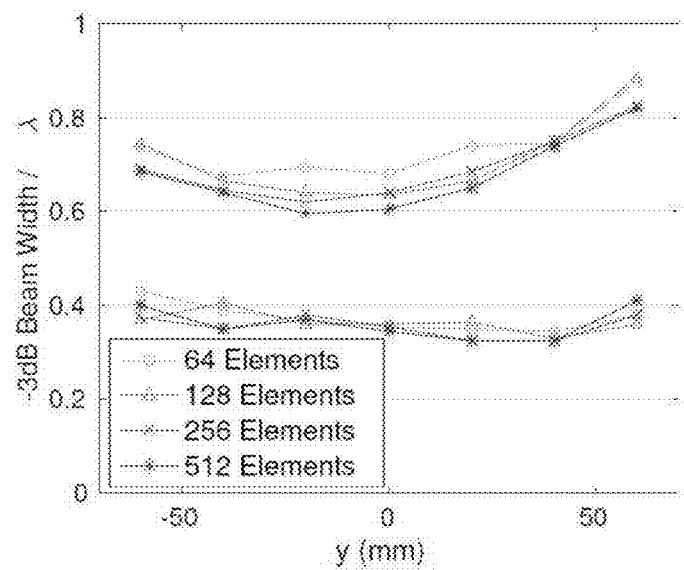
FIGS. 12A-I plot −3 dB beamwidth (A)-(C), the peak pressure (D)-(F), and the peak sidelobe ratio (G)-(I) as a function of array configuration, for arrays with 64, 128, 256, and 512 total array elements. The −3 dB beamwidths are plotted for the lateral (bottom line) and axial (top line) beamwidths.
Figure 12B:
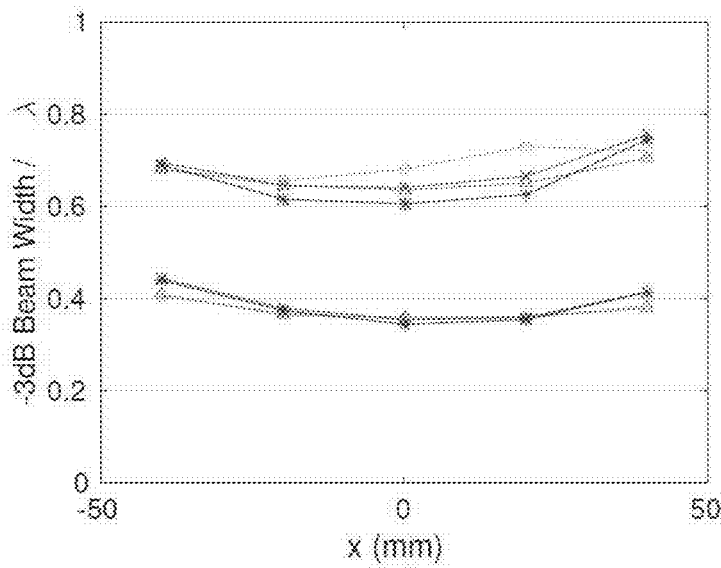
Figure 12C:
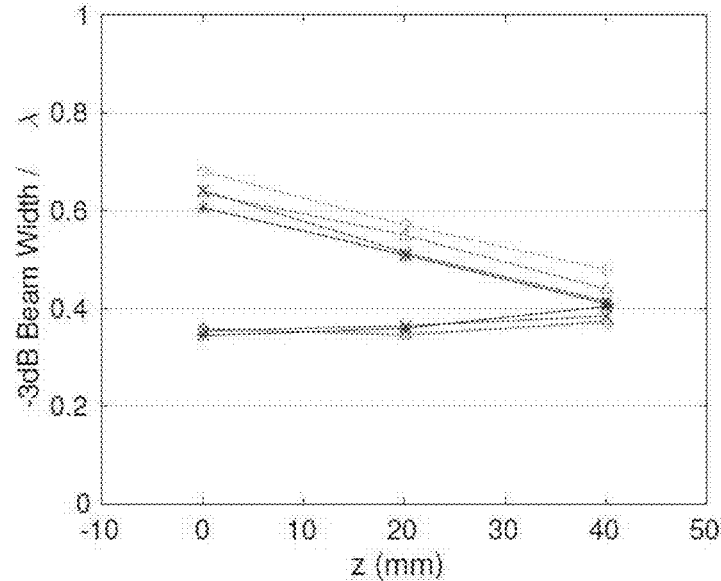
Figure 12D:
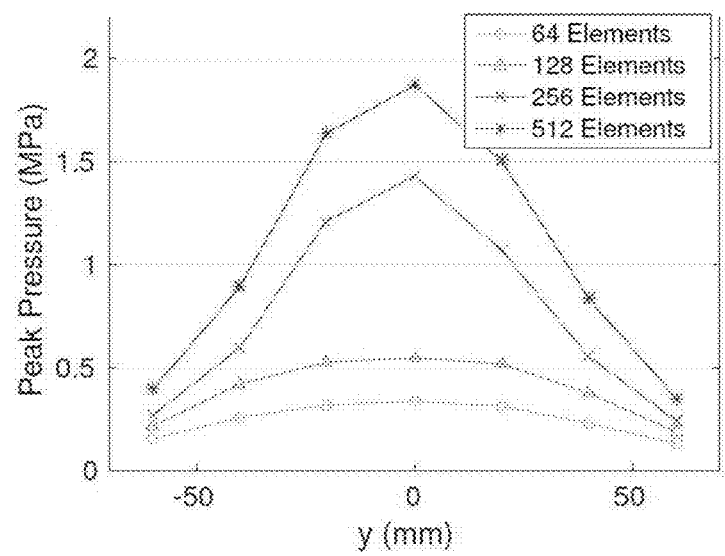
Figure 12E:
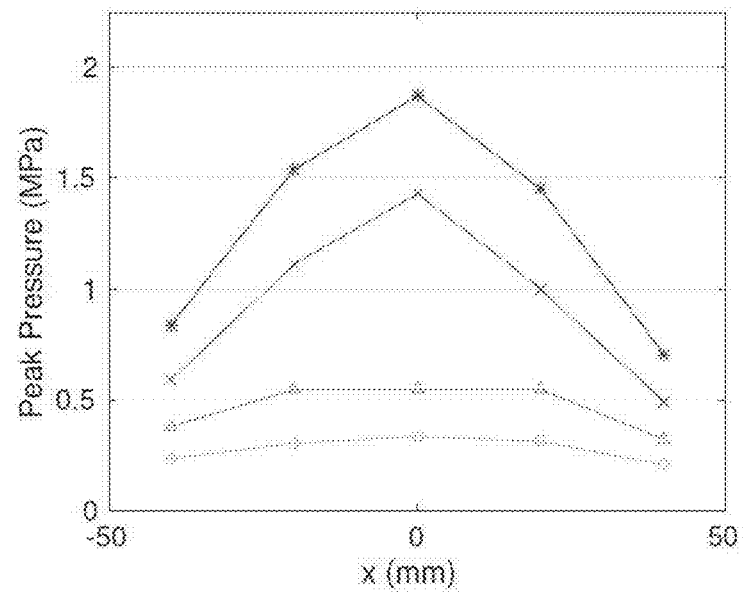
Figure 12F:
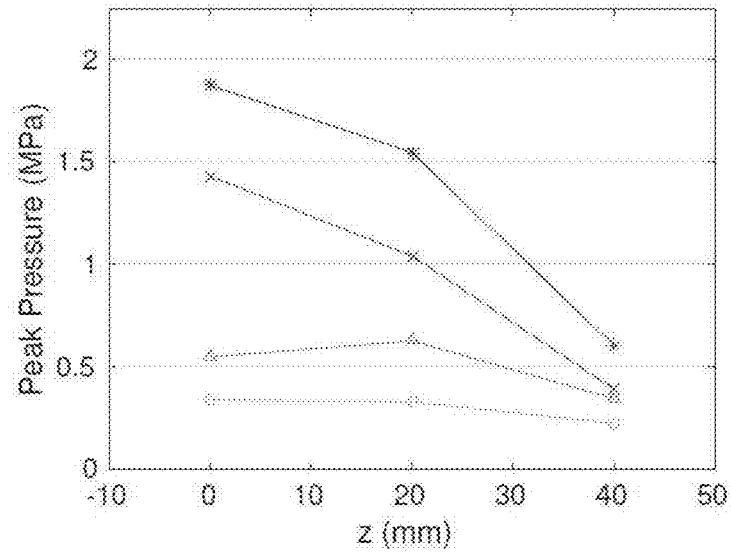
Figure 12G:
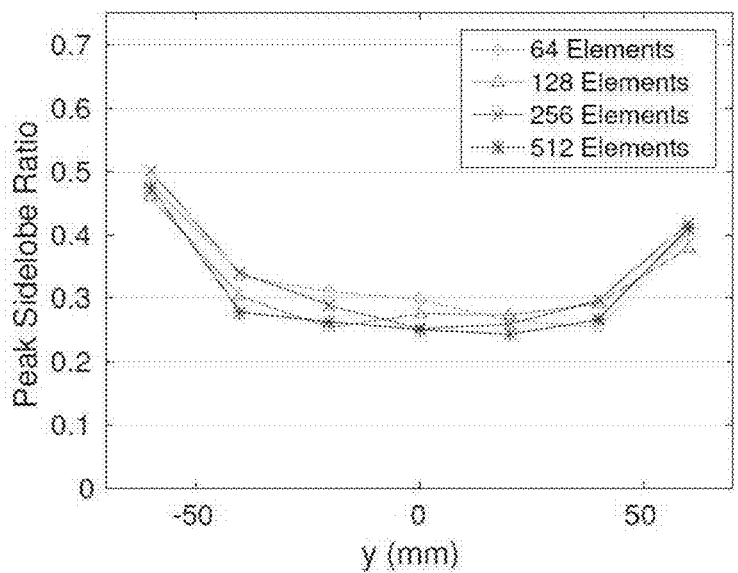
Figure 12H:
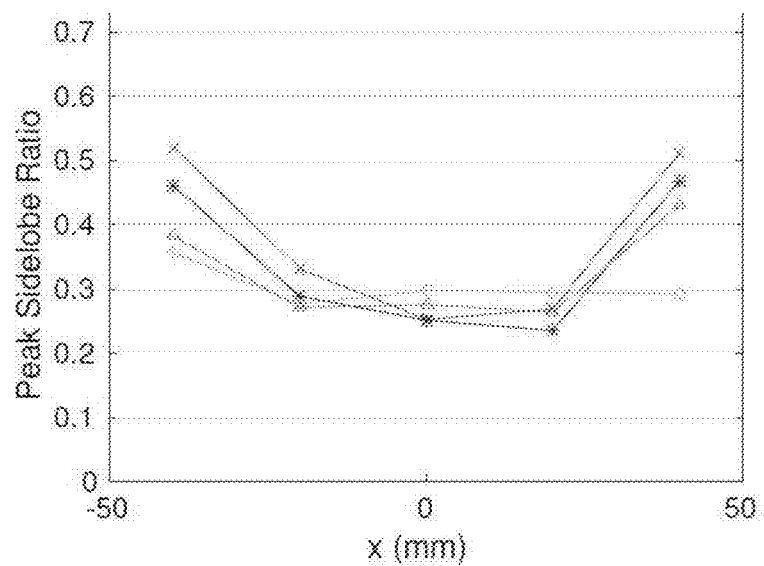
Figure 12I:
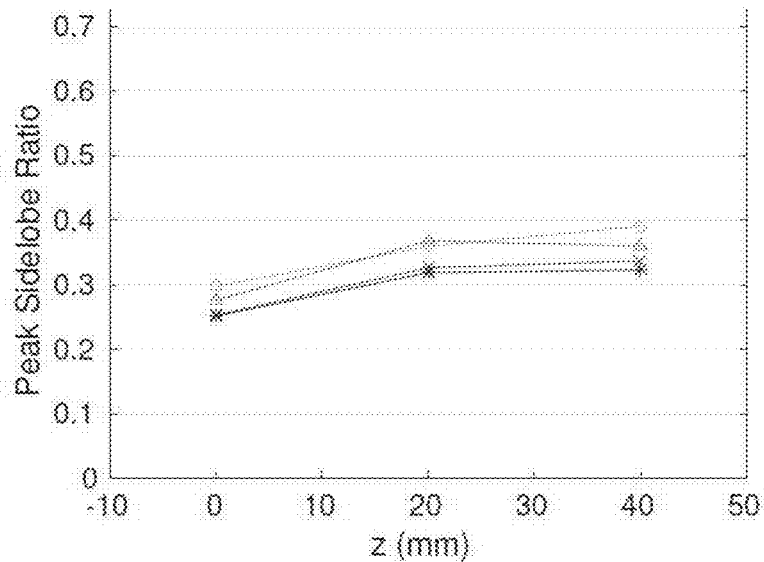

FIGS. 12A-1 illustrate the relationship between the number of array elements and the focusing quality of the array for steered locations in the x-, y- and z-directions at a frequency of 500 kHz. The total array power remains the same for all cases. FIGS. 12A-C show the effect of the number of elements on the ratio of the −3 dB beamwidth to the wavelength, I, at a number of different target locations. FIGS. 12D-F demonstrate the dependence of the peak acoustic pressure at each target location on the number of array elements. FIGS. 12G-I demonstrate the dependence of the peak sidelobe ration at each target location on the number of array elements. As can be seen, the peak pressure increases as the number of elements is increased, while there is negligible difference in the −3 dB beamwidth and peak sidelobe ratio, even at lateral positions within the head.

FIGS. 12A-C and 12G-1 show that the −3 dB beamwidths and the peak sidelobe ratio, respectively, remain relatively constant as a function of the number of elements in the array.

FIGS. 12D-F illustrate that the relative acoustic peak pressure at lateral points is highest for a 64-element array. Although it is also clear that the peak acoustic pressures at all points is lower for an array of fewer elements, it is also clear that for lateral points, there is little difference in peak acoustic pressure when using 64, 128, or 256 elements. It is intuitive that an array with more elements would achieve better focusing and have a higher steering range; however, it appears that when the far field of each beam lies within the brain, the steering performance is improved for even relatively small-number arrays.

Figure 13:
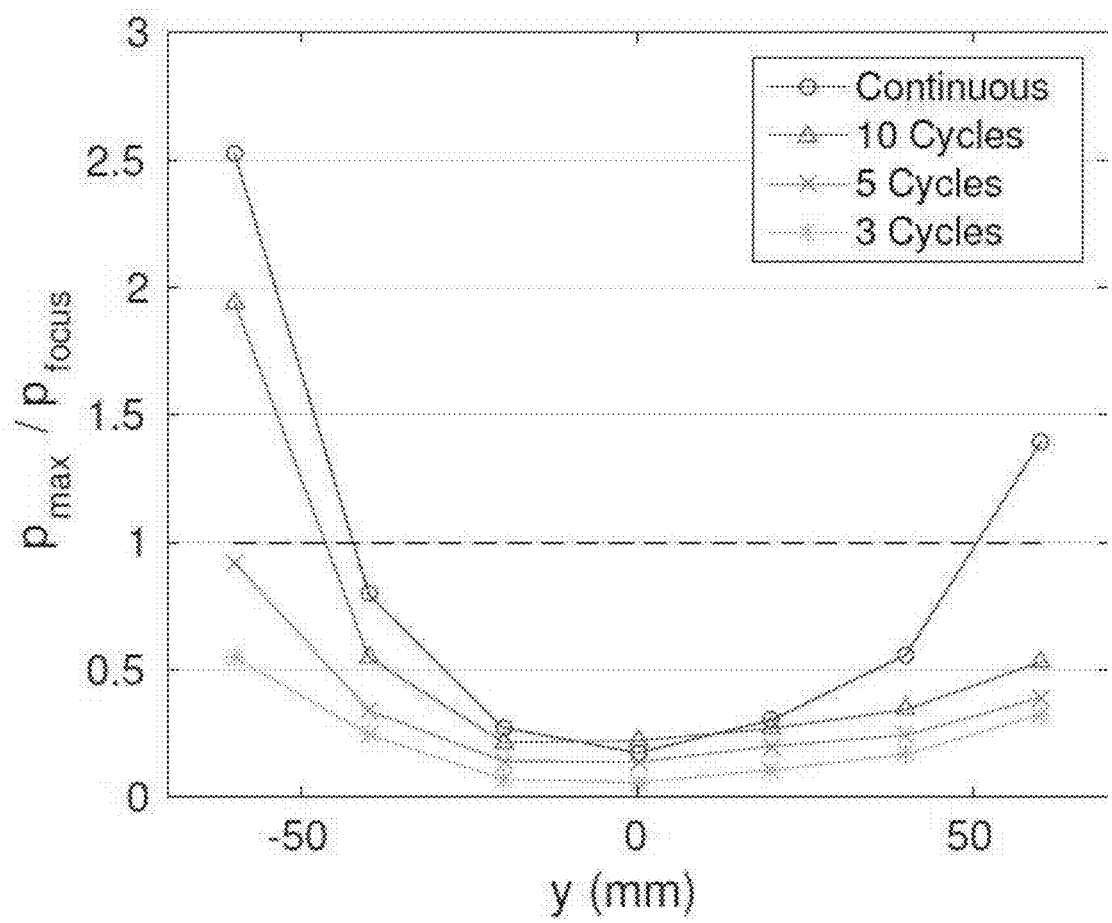
FIG. 13 plots the effect of longer pulse lengths on the focusing quality of the array.

FIG. 13 demonstrates the steering performance in the anterior-posterior direction for pulse lengths of 3, 5, and 10 cycles, as well as continuous wave excitation, when sonicating with a 256-element array at 500 kHz. It is clear that within 40 mm of the center of the skull cavity, it is possible to focus using any pulse length, however, at 6 cm in either direction, only short pulse lengths can be achieved with minimal deposition of acoustic energy elsewhere.

Example 5: Dual Frequency Excitation

A 256-element array sonicating was used to test the feasibility of dual-frequency excitation transcranially. Half (128) of the transcranial ultrasound transducer array elements were set to sonicate at 250 kHz, and half were set to sonicate at 500 kHz. The elements sonicating at each frequency were distributed evenly around the array, so that there was no concentration of elements sonicating at a single frequency.

Figure 14:
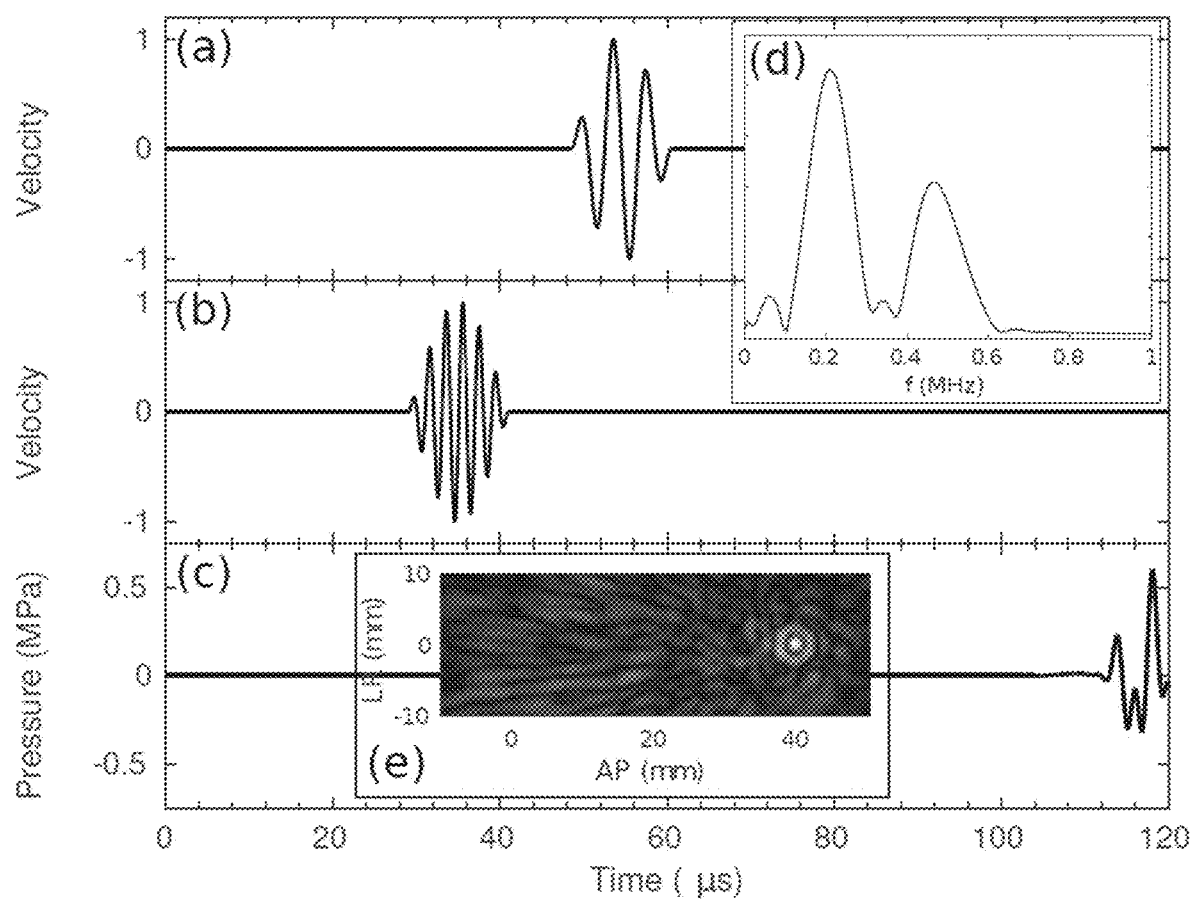
FIG. 14 plots simulated waveforms from dual frequency excitation. Waveforms (a) and (b) are emitted from 250 kHz and 500 kHz transducer, respectively, and waveform (c) shows the resultant received pulse at the focus. The inset (d) plots the time-averaged pressure at the focus, and the inset (e) plots the Fourier transform, illustrating two peaks corresponding to the excitation frequencies.

FIG. 14 shows the results from the dual-frequency simulation. Waveforms (a) and (b) plot the excitation pulses emitted from two transducers sonicating at (a) 250 kHz and (b) 500 kHz. Waveform (c) plots the response at the focus, showing the resultant dual frequency response. Inset (d) plots a Fourier transform of the received signal, showing peaks at 250 and 500 kHz, while inset (e) plots a 2D rendering of the normalized time-averaged pressure at the target.

Example 6: Safety Analysis

Since each transducer is focused inside the skull, the effect of high acoustic fields on skull integrity is a reasonable concern, and hence the effect of the transducer on the skull integrity was modeled to perform a safety analysis. To assess the thermal effects, the temperature rise resulting from acoustic pulses of variable lengths are simulated using the acoustic and thermal simulations. From the stable acoustic field generated by Equations 1 and 2, the absorbed power density in solid bone, Q is generated using Equation 4. The temperature map inside the skull is then simulated, with the temperature-time evolution governed by Equation 5. Using this thermometry data, the maximum pulse durations for a safe treatment were determined. In addition, in order to assess the potential safety of the sonications to brain tissue, the relative pressure at points on the inner surface of the skull were compared to the peak pressure amplitude at the focus, in order to assess the extraneous acoustic energy deposition away from the focus.

It was found that skull heating over relatively short pulses is negligible using this array design. Using a 256-element array sonicating at 100 W at a frequency of 500 kHz, a single 1000-cycle burst, representing a continuous wave sonication of duration 2 ms, led to a temperature rise of approximately 0.03° C. Naturally, a duty cycle lower than 100% would lead to a smaller temperature rise. With sufficient spacing to allow for skull cooling, in conjunction with present-day skull cooling mechanisms during treatment, it appears that skull heating would not be a limitation to potential treatments with this device.

Figure 15:
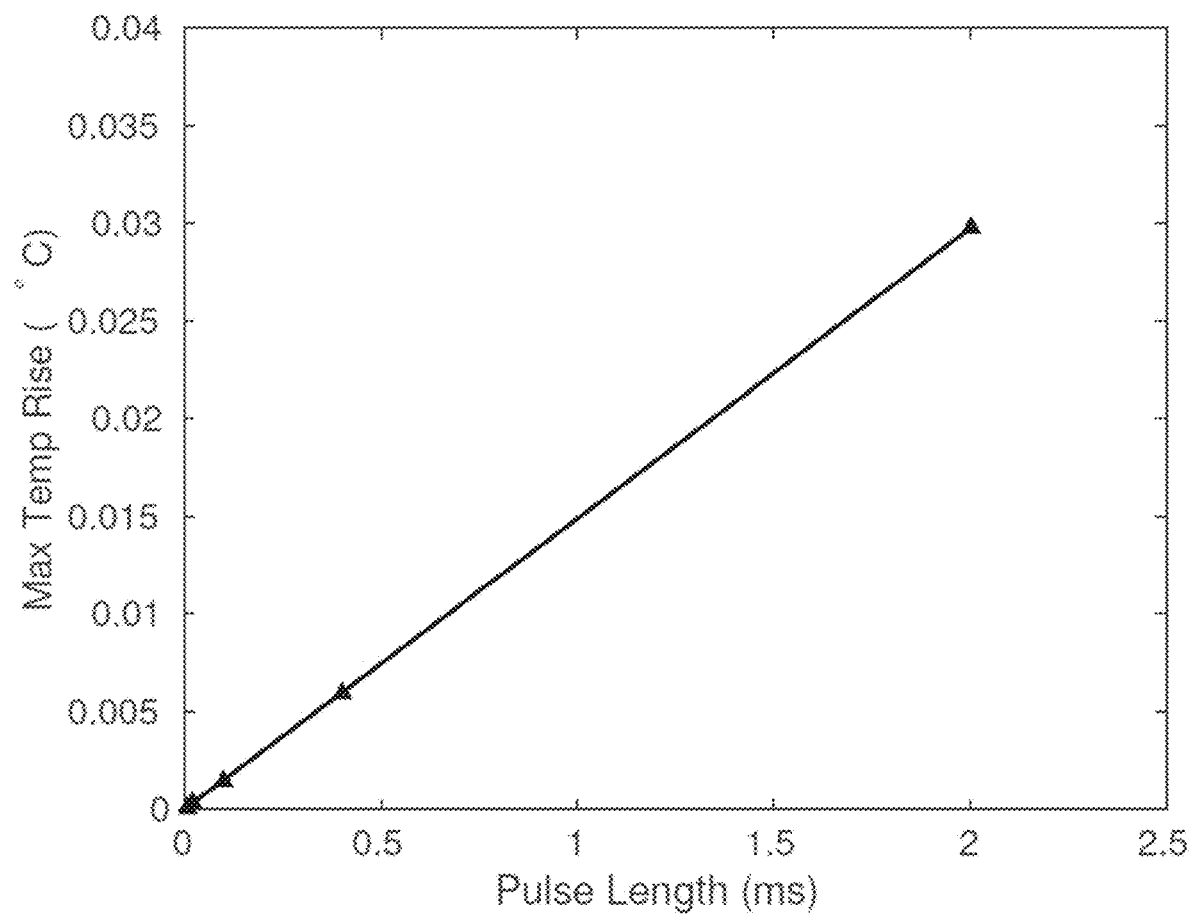
FIG. 15 plots the maximum temperature rise in the cranial bone when sonicating at 500 kHz, 100 W, for variable pulse lengths.

FIG. 15 is a plot of the simulated relationship between pulse length and the maximum temperature in the cranial bone in a 256-element array sonicating at 100 W at a frequency of 500 kHz. The markers on the line correspond to 3, 10, 50, 200, and 1000-cycle pulses. It is clear that for even relatively long pulses at relevant acoustic pressures, the model predicts that skull heating should be negligible.

Example 7: Multiple Frequency Insonation

The possibility of using variable frequencies for improved ultrasound transmission across different sections of the skull has been previously explored (White, Clement & Hynynen 2006). Since the presented array design transmits a localized plane wave across the skull, this array design is ideal for variable frequency transmission. Simulations were performed in which ultrasound was transmitted from the transducers of the array with frequency f, defined by $$f = \frac{mc}{2d}, \qquad (6)$$

where c is the average speed of sound in the bone across the transmission path, d is the thickness of the bone, and m>0 is an integer. The acoustic pressure at the target was then summed over all transducers n using the relation $$p = \Sigma_n p_n e^{i(2\pi f_n t)} \qquad (7)$$

for times t, where $f_n$ is the frequency of transducer n. Details of this derivation for focused ultrasound transmission through bone can be found in the appendix of White et al. (White P J, Hynynen K, Clement G T & Hynynen K, 2006 Ultrasound in Medicine & Biology 32(7), 1085-1096). A previously-introduced ray acoustic model was used to simulate the transmission of ultrasound through the skull (Jones R M, O'Reilly M A, Hynynen K, O'Reilly M a & Hynynen K, 2013 Physics in Medicine and Biology 58(14), 4981-5005). It was infeasible to transmit the ultrasound using a full-wave model, since the grid size was not small enough to accurately model the subtle changes in frequency required by this technique, and the ray acoustic model did not require re-discretization for different frequencies. The ray acoustic model simulated both the propagation of longitudinal and shear waves through the skull.

Figure 16A:
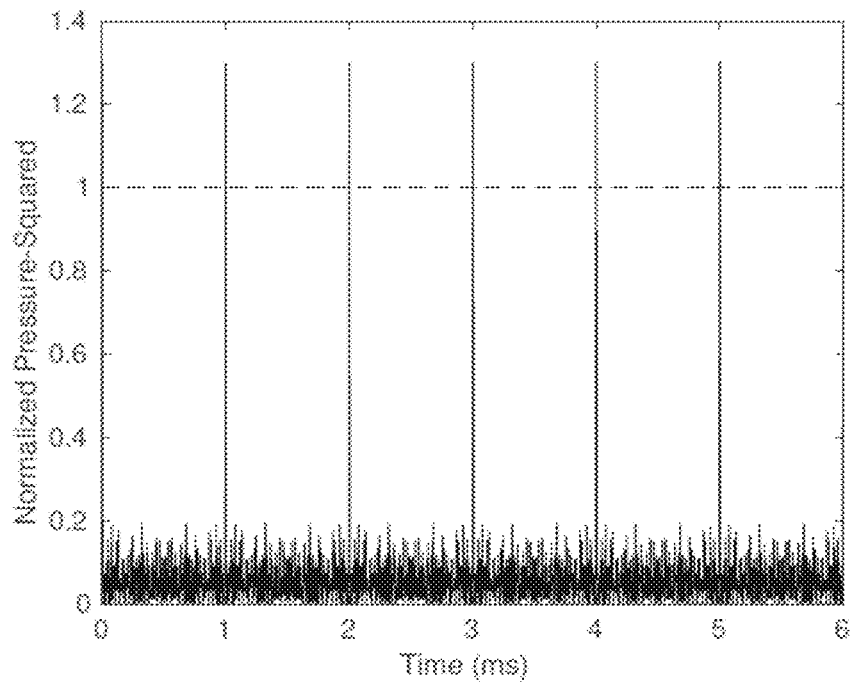
FIGS. 16A-B plot results from simulations of multiple frequency insonation, showing: (A) the resultant increase in ultrasound transmission when using variable frequencies (solid line) as compared to a single frequency (dashed line), shown for the unsteered case, and (B) the percentage change in the transmission intensity at different steered locations within the head.
Figure 16B:
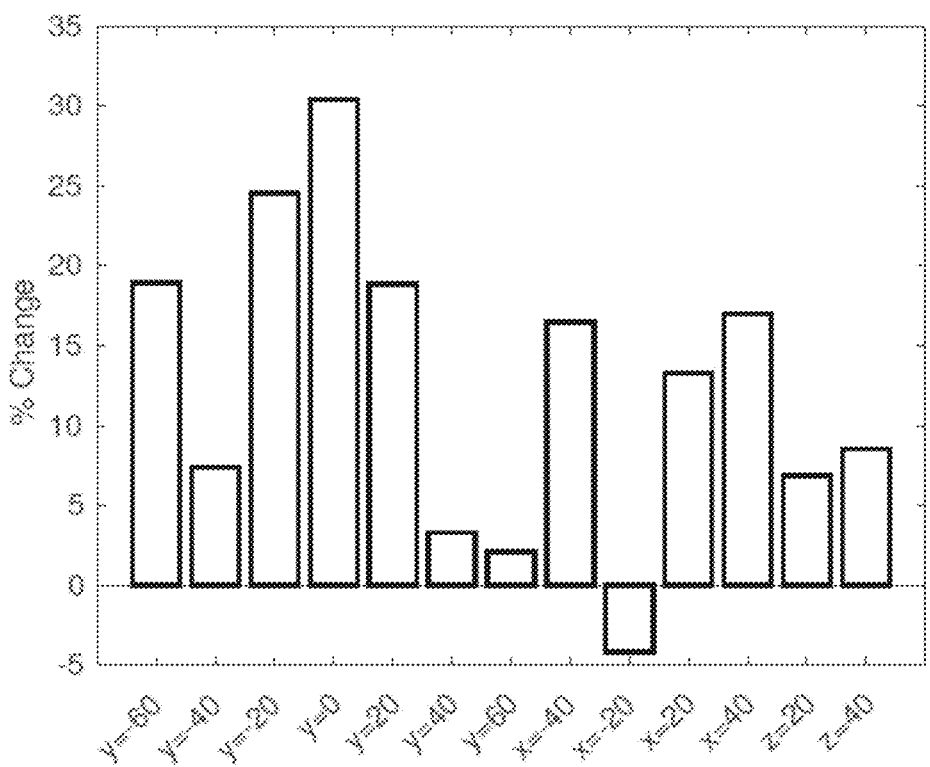

FIGS. 16A-B show results from these simulations, illustrating the potential for multi-frequency insonation. FIG. 16A plots the temporal pressure-squared, where the dashed line represents the single frequency insonation, and the solid line represents the multiple frequency insonation. The majority of the acoustic power is much lower than the single frequency case, since the constructive interference only occurs as the greatest common factor of the frequencies used in the array, while the peak acoustic power is 30% higher for brief periods of constructive interference. Accordingly, in some example embodiments, by timing the emissions from the different elements in the array using a burst sequence, it would be possible to obtain a reasonable duty cycle of constructive interference with multiple frequencies.

FIG. 16B illustrates the percentage changes in the acoustic power at the focus for the steered locations outlined in FIGS. 7A-B. In all cases except for steered location x=−20, the power transmission increases. The high variability in acoustic power at different points across the skull is indicative of different skull thicknesses, and potentially non-parallellity between the inner and outer surfaces of the skull at different locations.

Example 8: Variable Duty Cycle

Figure 17:
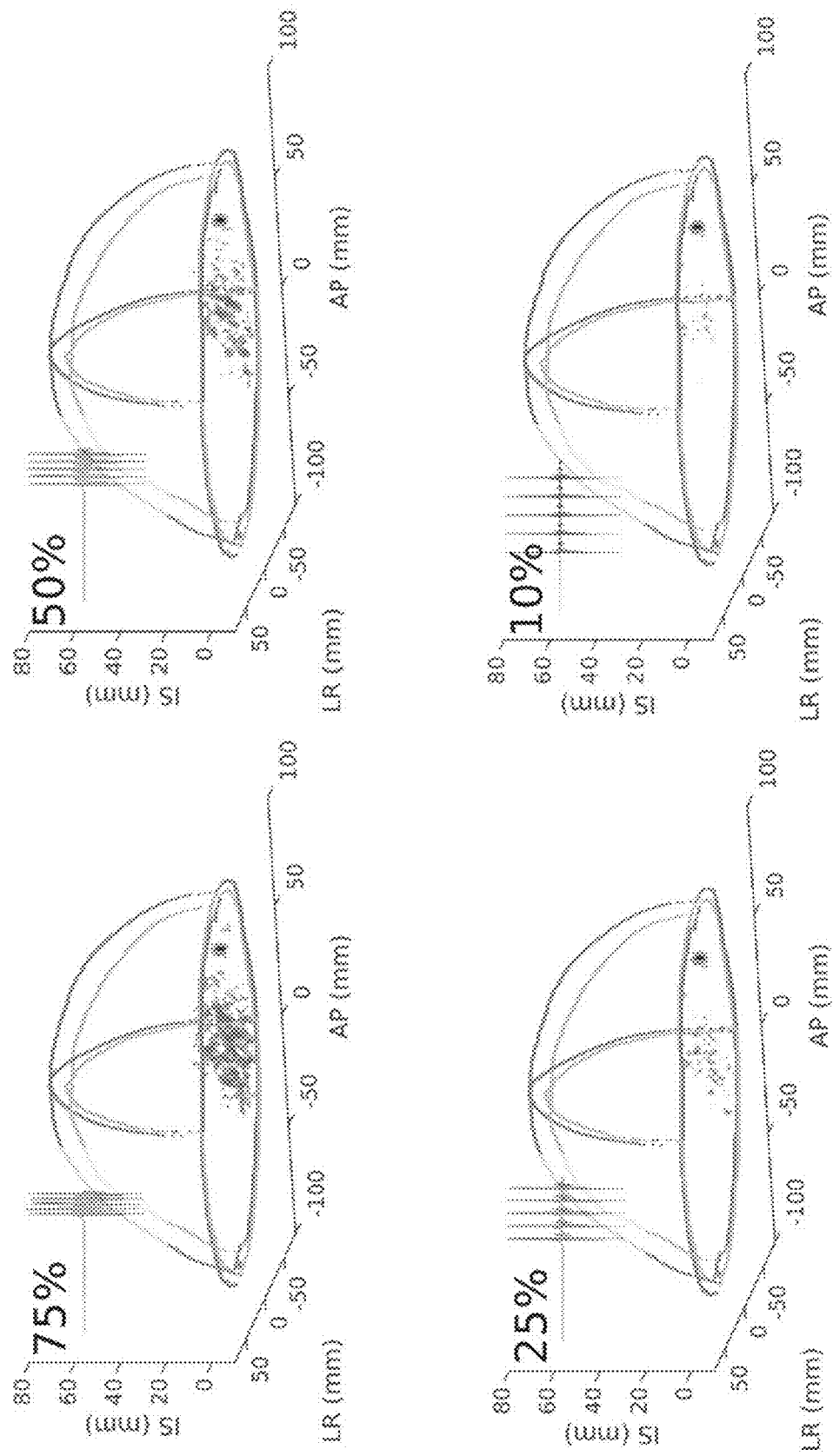
FIG. 17 demonstrates the effect of the duty cycle on focusing quality for 75, 50, 25, and 10% duty cycles. Illustrated are the −3 dB isosurfaces (dark gray) and the −6 dB isosurfaces (light gray), along with the received temporal acoustic signal at the focus, when steering 60 mm anterior to the center of the brain.

By varying the duty cycle of the bursts that are sent to the target, it is possible to determine how close the individual pulses can be within each burst. FIG. 17 illustrates the effect of 10, 25, 50, and 75% duty cycle on the focusing quality. The −6 dB isosurfaces in each case are illustrated in translucent red, while the −3 dB isosurfaces are illustrated in solid blue. The focusing quality improves noticeably when reducing the duty cycle from 75 to 10%.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A system for performing diagnostic or therapeutic transcranial ultrasound procedures, the system comprising:
   a support frame configured for placement around a head of a patient, said support frame comprising a plurality of transcranial ultrasound transducer array elements; and
   control and processing hardware operably connected to said plurality of transcranial ultrasound transducer array elements, said control and processing hardware comprising at least one processor and associated memory, said memory comprising instructions executable by said at least one processor for performing operations comprising:
      controlling said plurality of transcranial ultrasound transducer array elements, such that:
         each transcranial ultrasound transducer array element generates and focuses a respective ultrasound pulse at a respective primary focus, the respective primary foci of said plurality of transcranial ultrasound transducer array elements being spatially separated from one another; and far field regions respectively associated with said plurality of transcranial ultrasound transducer array elements spatially overlap within a far field overlap region located within a brain of the patient, the far field overlap region residing beyond each of the primary foci;

wherein a timing of the ultrasound pulses is controlled, based on registration data spatially registering positions and orientations of said plurality of transcranial ultrasound transducer array elements with volumetric image data associated with the patient, such that the ultrasound energy from the plurality of ultrasound pulses is collectively focused at a secondary focus residing within the far field overlap region via spatial and temporal alignment of the ultrasound pulses.

2. The system according to claim 1 wherein said support frame comprises:

an outer support portion supporting said plurality of transcranial ultrasound transducer array elements; and an inner coupling layer having an outer surface residing adjacent to an inner surface of said outer portion, said inner coupling layer having an inner surface configured to contact the head of the patient to facilitate coupling of acoustic energy between said transcranial ultrasound transducer array elements and the head of the patient.

3. The system according to claim 1 wherein said transcranial ultrasound transducer array elements are supported and controlled such that respective primary foci of said plurality of transcranial ultrasound transducer array elements lie between inner and outer surfaces of a skull of the patient when said support frame is placed around the head of the patient.

4. The system according to claim 1 wherein said plurality of transcranial ultrasound transducer array elements are supported relative to said support frame such that a respective beam axis of each transcranial ultrasound transducer array element is approximately normal to surface of a skull of the patient when said support frame is placed around the head of the patient.

5. The system according to claim 1 wherein said plurality of transcranial ultrasound transducer array elements are supported relative to said support frame such that a respective beam axis of each transcranial ultrasound transducer array element is oriented within ten degrees of a respective local surface normal vector associated with a skull of the patient when said support frame is placed around the head of the patient.

6. The system according to claim 1 wherein said plurality of transcranial ultrasound transducer array elements are supported relative to said support frame such that a respective beam axis of each transcranial ultrasound transducer array element is oriented within plus or minus five degrees of a respective local surface normal vector associated with a skull of the patient when said support frame is placed around the head of the patient.

7. The system according to claim 1 wherein one or more of said plurality of transcranial ultrasound transducer array elements are provided as a phased transducer sub-arrays.

8. The system according to claim 1 wherein one or more of said plurality of transcranial ultrasound transducer array elements are single-element ultrasound transducers.

9. The system according to claim 8 wherein said single-element ultrasound transducers are supported such that wavefronts respectively generated by said single-element ultrasound transducers are planar when propagating through at least a portion of a skull of the patient, between inner and outer surfaces of the skull, when said support frame is placed around the head of the patient.

10. The system according to claim 8 wherein one or more of said single-element ultrasound transducers are concave ultrasound transducers.

11. The system according to claim 1 wherein said support frame is configured to conform to an anatomical curvature of a portion of a skull of the patient, said support frame having been fabricated based on the volumetric image data associated with the patient.

12. The system according to claim 1 wherein said support frame comprises attachment interfaces for securing said plurality of transcranial ultrasound transducer array elements.

13. The system according to claim 12 wherein each attachment interface is configured to receive and support a transducer module comprising a sub-array of transducers.

14. The system according to claim 13 wherein each transducer module further comprises at least one imaging transducer configured to receive reflections from the patient's skull.

15. The system according to claim 1 wherein said support frame further comprises one or more fiducial markers attached thereto, and wherein said system further comprises:

a tracking system configured to detect signals from said fiducial markers and determine a spatial position and orientation of said support frame within an intraoperative reference frame; and a guidance user interface configured to display spatially registered volumetric images for image-guided procedures.

16. The system according to claim 1 wherein said plurality of transcranial ultrasound transducer array elements are removable.

* * * * *